United States Patent
Moskovits et al.

(10) Patent No.: US 7,898,658 B2
(45) Date of Patent: Mar. 1, 2011

(54) PLATFORM FOR CHEMICAL AND BIOLOGICAL SENSING BY SURFACE-ENHANCED RAMAN SPECTROSCOPY

(75) Inventors: Martin Moskovits, Santa Barbara, CA (US); Seung Joon Lee, Santa Barbara, CA (US); Ioana Pavel, Dayton, OH (US)

(73) Assignee: The Regents of the University of California, Oakland, CA (US)

( * ) Notice: Subject to any disclaimer, the term of this patent is extended or adjusted under 35 U.S.C. 154(b) by 473 days.

(21) Appl. No.: 12/018,763

(22) Filed: Jan. 23, 2008

(65) Prior Publication Data
US 2008/0174775 A1 Jul. 24, 2008

Related U.S. Application Data
(60) Provisional application No. 60/897,210, filed on Jan. 23, 2007.

(51) Int. Cl.
G01J 3/44 (2006.01)
(52) U.S. Cl. ...................................................... 356/301
(58) Field of Classification Search ................. 356/301, 356/244
See application file for complete search history.

(56) References Cited

U.S. PATENT DOCUMENTS
| | | | | |
|---|---|---|---|---|
| 6,149,868 A * | 11/2000 | Natan et al. | ................... | 356/301 |
| 6,406,777 B1 * | 6/2002 | Boss et al. | ................... | 356/301 |
| 2004/0023046 A1 * | 2/2004 | Schlottig et al. | ............ | 428/469 |
| 2006/0038990 A1 * | 2/2006 | Habib et al. | ................. | 356/301 |
| 2006/0055922 A1 * | 3/2006 | Li et al. | ....................... | 356/301 |
| 2006/0060472 A1 * | 3/2006 | Tomita et al. | ................ | 205/112 |

OTHER PUBLICATIONS
Al-Mawlawi, D., et al. Nanowires formed in anodic oxide nanotemplates. Journal of Materials Research. 1994, vol. 9, No. 4, pp. 1014-1018.

Baker, G., et al. Progress in plasmonic engineering of surface-enhanced Raman-scattering substrates toward ultra-trace analysis. Analytical and Bioanalytical Chemistry. 2005, vol. 382, pp. 1751-1770.

Bosnick, K., et al. Fluctuations and local symmetry in single-molecule Rhodamine 6G Raman scattering on silver nanocrystal aggregates. The Journal of Physical Chemistry B. 2002, vol. 106, pp. 8096-8099.

Drachev, V., et al. Nonlinear optical effects and selective photomodification of colloidal silver aggregates. Topics Appl Phys. 2002, vol. 82, pp. 113-148.

Eliasson, C., et al. Multivariate evaluation of doxorubicin surface-enhanced Raman spectra. Spectrochimica Acta Part A. 2001, vol. 57, pp. 1907-1915.

(Continued)

*Primary Examiner* — Kara E Geisel
(74) *Attorney, Agent, or Firm* — Carol L. Francis; Bozicevic, Field & Francis LLP

(57) ABSTRACT

Methods of analysis, and compositions relating to such, to determine the presence or absence of an analyte in a sample utilizing a composite substrate which facilitates surface enhanced Raman spectroscopy through the use of 'hot spots' of the form 'metal/analyte/metal' are presented. Additionally, substrates which contain 'hot spots' of the form 'metal/analyte/metal' and substrates which facilitate the formation of 'hot spots' of the form 'metal/analyte/metal' are presented as well as methods for making these substrates.

38 Claims, 13 Drawing Sheets

OTHER PUBLICATIONS

Emory, S., et al. Direct observation of size-dependent optical enhancement in single metal nanoparticles. Journal of the American Chemical Society. 1998, vol. 120, pp. 8009-8010.

Futamata, M., et al. Local electric field and scattering cross section of Ag nanoparticles under surface plasmon resonance by finite difference time domain method. The Journal of Physical Chemistry B. 2003, vol. 107, pp. 7607-7617.

Futamata, M., et al. Adsorbed sites of individual molecules on Ag nanoparticles in single molecule sensitivity-surface -enhanced Raman scattering. The Journal of Physical Chemistry B. 2004, vol. 108, pp. 13119-13127.

Garcia-Vidal, F., et al. Collective theory for surface enhanced Raman scattering. Physical Review Letters. 1996, vol. 77, No. 6, pp. 1163-1166.

Gresillon, S., et al. Experimental observation of localized optical excitations in random metal-dielectric films. Physical Review Letters. 1999, vol. 82, No. 22, pp. 4520-4523.

Gunnarsson, L., et al. Optimizing nanofabricated substrates for surface enhanced Raman scattering. Nanostructured Materials. 1999, vol. 12, pp. 783-788.

Kneipp, K., et al. Population pumping of excited vibrational states by spontaneous surface-enhanced Raman scattering. Physcial Review Letters. 1996, vol. 76, No. 14, pp. 2444-2447.

Kneipp, K., et al. Single molecule detection using surface-enhanced Raman scattering (SERS). Physical Review Letters. 1997, vol. 78, No. 9, pp. 1667-1670.

Kneipp, K., et al. Detection and identification of a single DNA base molecule using surface-enhanced Raman scattering (SERS). Physical Review E. 1998, vol. 57, No. 6, pp. R6281-R6284.

Krug, J., et al. Efficient Raman enhancement and intermittent light emission observed in single gold nanocrystals. Journal of the American Chemical Society. 1999, vol. 121, pp. 9208-9214.

Markel, V., et al. Near-field optical spectroscopy of individual surface-plasmon modes in colloid clusters. Physical Review B. 1999, vol. 59, No. 16, pp. 10903-10909.

Michaels, A., et al. Ag nanocrystal junctions as the site for surface-enhanced Raman scattering of single rhodamine 6G molecules. The Journal of Physical Chemistry B. 2000, vol. 104, pp. 11965-11971.

Moskovitz, M., et al. Surface-enhanced spectroscopy. Reviews of Modern Physics. 1985, vol. 57, No. 3, pp. 783-826.

Nie, S., et al. Probing single molecules and single nanoparticles by surface-enhanced Raman scattering. Science. 1997, vol. 275, pp. 1102-1106.

Otto, A., et al. Surface-enhanced Raman scattering. Journal of Physics: Condensed Matter. 1992, vol. 4, pp. 1143-1212.

Shalaev, V., et al. Optical properties of self-affine thin films. Physical Review B. 1996, vol. 54, No. 11, pp. 8235-8242.

Shalaev, V., et al. Nonlinear optics of random metal-dielectric films. Physical Review B. 1998, vol. 57, No. 20, pp. 13265-13288.

Stockman, M. Inhomogeneous eigenmode localization, chaos, and correlations in large disordered clusters. Physical Review E. 1997, vol. 56, No. 6, pp. 6494-6507.

Stuart, D., et al. Glucose sensing using near-infrared surface-enhanced Raman spectroscopy: Gold surfaces, 10 day stability, and improved accuracy. Analytical Chemistry. 2005, vol. 77, pp. 4013-4019.

Su, X., et al. Composite organic-inorganic nanoparticles (COINs) with chemically encoded optical signatures. NANO Letters. 2005, vol. 5, No. 1, pp. 49-54.

Xu, H., et al. Spectroscopy of single hemoglobin molecules by surface enhanced Raman scattering. Physical Review Letters. 1999, vol. 83, No. 21, pp. 4357-4360.

Xu, H., et al. Electromagnetic contributions to single-molecule sensitivity in surface-enhanced Raman scattering. Physical Review E. 2000, vol. 62, No. 3, pp. 4318-4324.

Aizpurua, et al. "Optical Properties of Gold Nanorings" Phys. Rev. Lett. 2003, 90:057401.

Crozier, et al. "Optical Antennas: Resonators for Local Field Enhancement" J. Appl. Phys. 2003, 94:4632-4642.

Genov, et al. "Resonant Field Enhancements from Metal Nanoparticle Arrays" Nano Lett. 2004, 4:153-158.

Gunnarsson, et al. "Confined Plasmons in Nanofabricated Single Silver Particle Pairs: Experimental Observations of Strong Interparticle Interactions" J. Phys. Chem. B 2005, 109, 1079-1087.

Hartschuh, et al. "High-Resolution Near-Field Raman Microscopy of Single-Walled Carbon Nanotubes" Phys. Rev. Lett. 2003, 90:95503.

Lai, et al. "Comparison of the Signaling and Stability of Electrochemical DNA Sensors Fabricated from 6- or 11-Carbon Self-Assembled Monolayers" Langmuir, 2006, 22:10796-10800.

Lee et al. "Hot Spots in Silver Nanowire Bundles for Surface-Enhanced Raman Spectroscopy" J. Am. Chem. Soc. 2006, 128:2200-2201 (published on web Jan. 26, 2006).

Lu, et al. "Nanophotonic Crescent Moon Structures with Sharp Edge for Ultrasensitive Biomolecular Detection by Local Electromagnetic Field Enhancement Effect" Nano Lett. 2005, 5:119-124.

Masuda, et al. "Ordered Metal Nanohole Arrays Made by a Two-Step Replication of Honeycomb Structures of Anodic Alumnia" Science 1995, 268:1466-1468.

* cited by examiner

PLATFORM FOR CHEMICAL AND BIOLOGICAL SENSING BY SURFACE-ENHANCED RAMAN SPECTROSCOPY

CROSS REFERENCE TO RELATED APPLICATIONS

This application claims the benefit under 35 U.S.C. §119 (e) of Prior U.S. provisional application Ser. No. 60/897,210 filed Jan. 23, 2007, the disclosure of which application is herein incorporated by reference.

INTRODUCTION

Surface-Enhanced Raman Spectroscopy (SERS) is an analytical technique based on an effect discovered in the 1970's. Briefly, SERS is a highly enhanced form of Raman spectroscopy, an optical analysis technique that can provide molecular identification and quantification by recording a spectrum that displays characteristic vibrational fingerprints of molecules or constituent parts of molecules. SERS is enabled when the molecules whose identity one wishes to determine (the analyte) reside in close proximity to a nanostructured metal surface (the SERS-active substrate or surface), which provides a significant increase in the intensity of the Raman spectrum over standard Raman spectroscopy. When the analyte resides in close proximity to two or more nanostructured metal surfaces, it forms a 'hot spot' of the form 'metal/molecule/metal' which provides an additional significant increase in the intensity of the Raman spectrum over a surface enhanced Raman spectrum where the analyte is in close proximity to only one nanostructured metal surface.

Two problems have prevented SERS, and especially 'hot spot' SERS, from becoming a powerful and routine analysis or medical diagnostic technology for detecting, for example, chemical or biological hazards, environmental toxins, or evidence of pathogens in body fluids. First, SERS-active substrates have, in general, been highly technical preparations that make it difficult to achieve repeatability, dependability and stability so as to ensure reproducible results sample-to-sample. Further, SERS-active substrates are not sufficiently robust to ensure adequate "shelf-life" and they are not amenable to easy routine use protocols to allow the analysis to be automated or to be carried out by technicians.

Second, the metals most often used as SERS substrates, gold and silver, are highly chemically-unspecific, hampering the ability of the technique to routinely exhibit specificity towards a target analyte in the presence of the many hundreds, or even thousands of background substances one encounters in body fluids or in the environment.

As a result, it is desirable to develop improved 'hot spot' SERS methods and substrates in order to improve repeatability, dependability, stability, and specificity.

SUMMARY

Methods of analysis, and compositions relating to such, to determine the presence or absence of an analyte in a sample utilizing a composite substrate which facilitates surface enhanced Raman spectroscopy through the use of 'hot spots' of the form 'metal/analyte/metal' are presented. Additionally, substrates which contain 'hot spots' of the form 'metal/analyte/metal' and substrates which facilitate the formation of 'hot spots' of the form 'metal/analyte/metal' are presented as well as methods for making these substrates.

BRIEF DESCRIPTION OF THE DRAWINGS

Certain embodiments of the invention will be further described with reference being made to the following drawings.

FIG. 2A: SEM images of BT-modified Ag-PAO templates obtained by partial dissolution of the alumina matrix in 0.1 M aqueous NaOH for (a) 0 s, (b) 210 s, (c) 270 s, and (d) 450 s. Adjacent images are 5× magnifications over the corresponding image. FIG. 2B: SEM image as in (a) of FIG. 2A, but for a larger portion of the template. FIG. 2C: SEM image as in (c) of FIG. 2A but imaged at a glancing angle.

DETAILED DESCRIPTION

Figure 1:
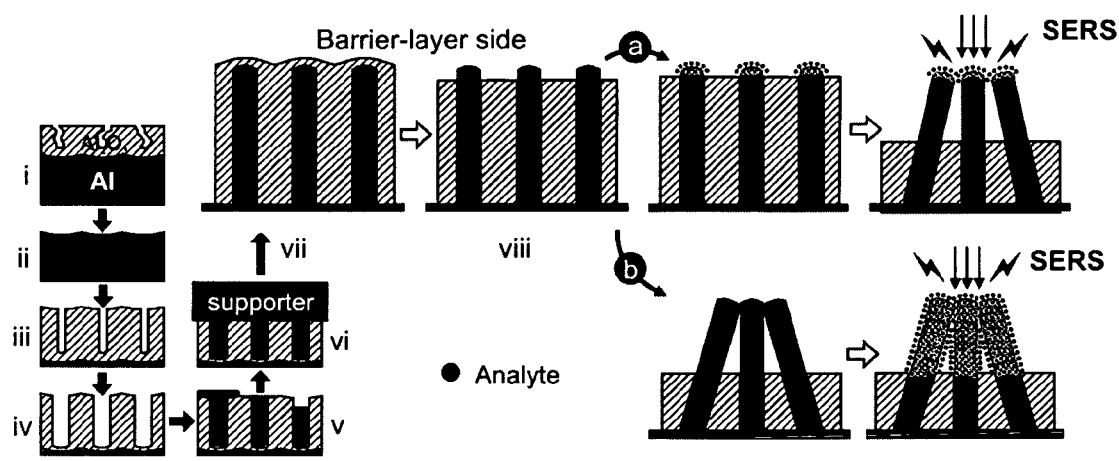
FIG. 1. Schematic drawing illustrating the preparation of Ag-PAO template (Panels i to viii) and its subsequent treatment to render it a SERS-active substrate. Schematic elements (a) and (b) illustrate the "add-analyte-then-etch" and the "etch-then-add-analyte" approaches, respectively. Panel i. shows a sheet of high-purity aluminum, with an irregular aluminum oxide coating. Panel ii. shows this sheet of aluminum after the layer of aluminum oxide has been removed. Panel iii. shows the porous aluminum oxide matrix formed from the aluminum sheet by Masuda's anodization process (Masuda, H.; Fukuda, K. *Science* 1995, 268, 1466-1468.) Panel iv. shows this matrix following additional anodization and pore-widening. Panel v. illustrates this matrix undergoing silver deposition by AC electrolysis. Panel vi. shows this silver-filled porous matrix glued to a silicon wafer on the oxide (pore) side of the matrix. Panel vii. shows this matrix flipped over, after the remaining aluminum has been removed from the aluminum oxide matrix. Panel viii. shows this matrix after the aluminum oxide has been partially etched away, exposing the tips of the silver nanowires. Element (a) illustrates adding benzenethiol to the exposed tips of the silver nanowires. The next panel shows SERS detection of the benzenethiol after additional etching which exposed a greater length of the silver nanowires allowing these nanowires to spatially collapse, bringing the tips of the wires close enough together to form a SERS hotspot. This sequence is called "add-then-etch." Element (b) illustrates etching the matrix, which allows the nanowires to spatially collapse, bringing the tips of the wires closer together. The next panel shows SERS detection of benzenethiol after it has been added to the nanowires which had already spatially collapsed. This sequence is called "etch-then-add."

Before embodiments of the present invention is described in greater detail, it is to be understood that the invention is not limited to particular embodiments described as such may, of course, vary. It is to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely", "only", and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method may be carried out in the order of events recited or in any other order which is logically possible.

Substrates

As used herein, the term "substrate" refers to both precursors to SERS-active substrates as well as SERS-active substrates, unless specifically indicated otherwise. In general, SERS-active substrates can be generated from precursor substrates The substrates described herein contain arrays of nanowires (e.g., silver nanowires) disposed in a matrix. Such can be produced by depositing SERS-active metal by electrochemical deposition, chemical vapor deposition, electrodeless deposition or any other suitable method inside the pores of a nanoporous matrix, such as porous anodic aluminum oxide (PAO), or any other template or matrix in which a surface-enhanced-Raman-active metal, such as silver, gold, copper, platinum or indium can be deposited in the form of nano- or microwires. In the substrate precursor form, the nanowires are held in position relative to one another by the material of the matrix; SERS-active substrates are formed by treatment of the substrate precursor so as to bring at least two surfaces of SERS-active metal, where at least on surface is on the nanowires into proximity sufficient to generate a SERS signal. The two surfaces can be provided by adjacent nanowires, by a nanowire and a nanoparticle, and/or, in embodiments in which the nanowires include a nanohole at the nanowire tip, by surfaces defining the nanohole of a nanowire.

In general, substrates are relatively planar, with pores in the matrix extending into the matrix from at least one side of the plane of the substrate. The pores in this matrix are approximately normal to the plane of the substrate, resulting in surface-enhanced-Raman-active metal nano- or microwires that extend into the substrate approximately normal to the plane of the substrate.

The nanowires can, but do not need to, extend all the way through the depth of the matrix. If the wires do not extend all the way through the matrix, one end of these nanowires may be covered by a first material, while the other end of the wires is not covered by the matrix. In such a substrate, the side of the substrate where the first material covers the wire ends is the "closed pore" side, and the side of the substrate where the first material does not cover the wire ends is the "open-pore" side.

The open-pore side of the substrate can be covered with an additional layer. This layer can act to protect the integrity of the metal wires, and can optionally provide a base for the substrate for subsequent handling and use. For example, the open-pore side of the substrate can be epoxy-glued to a silicon wafer, which not only isolates the metal nanowires from the environment, but also provides a relatively inert base for the substrate to sit on during subsequent use. Further, this additional layer can serve to inhibit exposure of nanowires from the surface it covers (e.g., the additional layer can serve as a "base" so as to inhibit removal of matrix material from the covered surface during etching.)

In general, substrates can be described as having a first surface and a second surface, wherein at least the first surface which lies over (e.g., when in a precursor substrate) and/or defines (e.g., when in SERS-active substrate form) pores in which deposits of SERS-active metal are disposed in the matrix. The second surface, which is opposite the first surface, can serve as a "base" such that when a precursor substrate is treated to produce a SERS-active substrate, the nanowires of the SERS-active substrate extend away from the second surface (see, e.g., FIG. 1). The second surface of the substrate can be composed of the same or different material as the matrix.

While residing within the matrix, the material of the matrix facilitates protection of the nanowires, making the nanowires resistant to surface contamination or reaction. This bestows a long shelf-life to the substrate (e.g., up to six months) under ambient conditions. The shelf-life can be enhanced by providing a protective agent to further shield the nanowires and, optionally the matrix from the environment, e.g., by use of a suitable plastic cover or packaging, which can be adapted to provide for hermetically sealing the substrate in a suitable package. As used herein nanowires of a precursor of a SERS-active substrate are often referred to as "deposits", reflecting the positioning of the SERS-active metal of the nanowires within pores of the substrate.

The surfaces of the nanowires of the substrate are spaced so that when in the form of a SERS-active substrate, they reside in close proximity to a nanostructured metal surface (the SERS-active substrate or surface), which provides a significant increase in the intensity of the Raman spectrum over standard Raman spectroscopy. The nanowire surfaces can be brought into close proximity by, for example, collapse of nanowires toward one another so as to bring outer nanowire surfaces into proximity, e.g., to form "hot spots" or "bundles" as described below. Alternatively, or in addition, the surfaces defining a nanohole at a tip of a nanowire can provide for this proximity effect. In both situations, the proximity of the SERS-active surfaces provides for an increase in Raman signal intensity. This increase in Raman signal intensity has been observed for inter-surface distances up to about 200 nm. This increase in signal intensity is generally greater for smaller inter-surface distances.

Since detection of an analyte molecule involves the analyte being inserted between these SERS-active surfaces, the inter-surface distance should be at least as large as the smallest cross-section of the analyte to be detected. Thus, the minimum inter-surface distance is on the order of a few angstroms. The spacing between nearest neighbor nanowires in the matrix range from approximately 10 nm to 200 nm, depending on the conditions used for their preparation. The distance between surfaces of a SERS-active metal to provide signal enhancement over a single SERS particle is generally from about 10-200 nm, with distances as small as 0.5 nm between surfaces being of interest. Analytes of which all or at least a portion can be inserted into such spaces are thus of interest.

The nanowires formed form the deposits of the matrix can vary in length. In general, nanowires can be of a length from about 100 nm to hundreds of microns (e.g., 100 microns, 200 microns, 300 microns, 400 microns, or more). Accordingly, the depth of the pores in the matrix of substrate in which the deposits are disposed can similarly vary in length.

In a SERS-active substrate, there exist areas where particles of surface-enhanced-Raman-active metal are in close enough proximity that, when associated with an analyte either directly or via a specific recognition molecule, SERS 'hot spots' of the form metal/analyte/metal can be formed. Precursors to SERS-active substrates differ from SERS-active substrates in that the deposits of surface-enhanced-Raman-active metal are not close enough together in the precursors to form SERS 'hot spots' when associated with an analyte. Precursors to SERS-active substrates are treated to form SERS-active substrates.

Prior to such treatment, these precursor substrates may or may not be contacted with a sample suspected of containing an analyte molecules and/or contacted with a specific recognition molecule for association (e.g., covalent or non-covalent (e.g., absorption)) with the SERS-active metal of the metal deposits in the matrix that become exposed during such treatment. Thus, optionally, the substrates (either in precursor or SERS-active form) can be provided in a composition with one or more of a specific recognition molecule, an analyte of interest (e.g., to serve as a control), and/or a sample suspected of containing an analyte of interest. Alternatively, recognition molecules, analytes of interest, and/or samples can be added to the substrate during the SERS-active substrate production process. Stated differently, the methods and compositions disclosed herein contemplate both those involving methods based on the etch-then-add-analyte and add-analyte-then-etch methods disclosed herein.

Production of SERS-active substrates from a precursor substrate can be accomplished by removing matrix material to expose the nanowires and/or by extending the nanowires from the matrix surface (e.g., through use of nanoparticles or metal exchange.)

For example, where a SERS-active substrate is produced from a precursor by exposing the nanowires relative to a surface of the substrate. This can be accomplished by, for example, removing matrix material away from the deposits (e.g., by removing matrix material horizontally relative to the base of the substrate). In this example, the matrix material (sometimes referred to herein as a first material of the substrate) is differentially removable from the substrate relative to the deposits of surface-enhanced-Raman-active metal (sometimes referred to herein as the second material of the substrate). Removal of the matrix material exposes the deposits, provide for SERS-active nanowires. The first material can be differentially removable by, for example, being differentially etchable from the substrate relative to the deposits of surface-enhanced-Raman-active metal.

Production of the SERS-active substrate from a precursor substrate can also involve expanding the pores of the matrix to as to expose the nanowires so as to allow the exposed nanowires to come into close proximity. The pores in the first material can also be elongate. The pores may be quite elongate, with aspect ratios of ten or more.

Alternatively or in addition, the SERS-active substrate can be generated such that the substrate includes nanowires having tips that define a nanohole. "Nanohole" as used herein refers to a depression in an exposed tip of a nanowire. The surfaces defining this depression thus serve as SERS-active metal surfaces which can provide for a SERS signal. The depression of the nanohole can be of any suitable shape and size, and is generally designed so as to accommodate at least a portion of an analyte to be detected. It will be appreciated that the interior surface defining the depression of the nanohole can be modified in any suitable manner described herein for nanowires. For example, the nanohole surface can be modified to include a specific recognition molecule, as discussed in more detail below.

Alternatively or in addition, a SERS-active substrate can be generated from a precursor substrate by capping deposits of surface-enhanced-Raman-active metal exposed on the first surface with deposits of a second surface-enhanced-Raman-active metal. These second metal deposits are more closely spaced than the pores of the matrix. These second metal deposits may be of any surface-enhanced-Raman-active metal, such as copper, gold or silver.

Additionally, the deposits of surface-enhanced-Raman-active metal can extend beyond the surface of the first material. These deposits may extend beyond the surface of the material as nanowires. These nanowires can be capable of spontaneously spatially condensing relative to one another, such that the nanowires get closer to each other than the inter-pore distance. Further, the metal of these nanowires can be associated with a target analyte, or with a specific recognition molecule, which specifically reacts with a target analyte.

Alternatively or in addition, the substrate can comprise surface-enhanced-Raman-active metal nanoparticles linked to the metal deposits via ligands. Such nanoparticles can be used to facilitate production of a SERS-active substrate from a precursor substrate by contacting a substrate having deposits exposed on a first surface with the nanoparticles under suitable conditions to provide for linking the nanoparticles to the exposed deposits. Examples of nanoparticles include, but are not necessarily limited to, gold, silver and copper nanoparticles.

In some cases, the surface-enhanced-Raman-active metal is any of a variety of suitable surface-enhanced-Raman-active metals, such as silver, gold, copper, platinum and indium. Combinations of surface-enhanced-Raman-active metals are also contemplated for use. Such a combination can be in the form of an alloy, as well as a simple mixture.

As noted above, the substrate may be combined with an analyte (e.g., to serve as a control) or with a sample suspected of containing a target analyte. Further, the substrate may be optionally exposed to a specific recognition molecule for the analyte prior to or after treatment to generate a SERS-active substrate. In general, the specific recognition molecule is a member of a binding pair that is capable of forming a complex of analyte-specific recognition molecule, such that the specific recognition molecule specifically reacts with the analyte of interest. Specific recognition molecules can be, for example, biomolecules (polymers that can be found in nature, such as nucleic acids, proteins), where the biomolecules can be produced by any suitable method (e.g., naturally occurring, recombinant, or chemical synthesis methods).

For example, if the targeted analyte is a polynucleotide (e.g., DNA or RNA), a nucleic acid probe (e.g., a short single-stranded oligonucleotide complimentary to at least a portion of one of the strands of the target nucleic acid sequence) may be used as a specific recognition molecule. Such a nucleic acid probe can attached to the SERS-active metal of the substrate by, for example, terminating an end of the nucleic acid probe with a group capable of binding to the SERS-active metal, for example a thiol or amine group. Other examples of specific recognition systems include, but are not necessarily limited to, DNA:DNA, RNA:RNA, DNA:RNA, aptamer:polypeptide, antigen:antibody, enzyme:ligand (e.g., where the ligand may be native or non-native to the enzyme, and may be a substrate or inhibitor), metal-organic complex:ligand, and other ligand:receptor systems (e.g., GPCR:ligand). In each of these cases either species can be used as a specific recognition molecule for detecting the other. For example, an antibody may be used as a specific recognition molecule for an antigen or an antigen may be used as a specific recognition molecule for an antibody. These specific recognition molecules may be covalently to surface-enhanced-Raman-active metal deposits through a variety of functional groups, including thioethers, amines, and carboxylate groups.

The substrate can comprise an agent capable of isolating the substrate from environmental hazards (e.g., contamination), which may be referred to herein as an "environmental agent" or "environmental protection agent". The environmental agent can be, for example, plastic, mylar, polyethylene glycol (PEG), or polyvinyl alcohol. The environmental agent may be in the form of a package, such as a pouch or box. This package may additionally be hermetically sealed, and can be filled with an inert gas, such as nitrogen or argon. Additionally or alternatively, the environmental agent may take the form of a removable layer, e.g., film or coating, over all or a portion of at least a surface of the precursor substrate to be used to generate a SERS-active substrate surface. Such a protective layer can be provided so as to be easily removable from the substrate without significantly damaging the substrate. Exemplary materials for such removable layers include polyethylene glycol and polyvinyl alcohol films. An environmental agent can be provided with a SERS-active substrate precursor so as to ease storage and handling of the substrate while avoiding significant damage or contamination. The environmental agent should be readily removable so that the substrate can be easily prepared for use. While residing within the matrix the metal deposits are impervious to surface contamination or reaction. This bestows a long shelf-life to the substrate. Additional packaging can further enhance protection from the environment, such as when the substrate precursor is hermetically sealed in suitable packaging.

Methods of Making Substrates

The present disclosure further provides methods of making substrates comprising filling the pores of a porous matrix with nanometer scale deposits of surface-enhanced-Raman-active metal. The pores of the matrix are nanometer in scale and the distance between the pores is nanometer in scale.

A SERS-active substrate precursor can be made by, for example, filling the pores of a matrix composed of a first material with SERS-active metal deposits. Pores can be filled by electrochemical deposition, chemical vapor deposition, electroless deposition or any other suitable means.

As noted above, production of a SERS-active substrate from a precursor substrate can be accomplished by differentially removing a portion of the first material, thereby exposing the deposits of surface-enhanced-Raman-active metal. Removal of the matrix material exposes the deposits as nanowires, and can provide for production of a SERS-active substrate.

Additionally, the substrate can be exposed to conditions appropriate for metal exchange (also known as Galvanic exchange, or Galvanic displacement) with a surface-enhanced-Raman-active metal which is less electropositive than the metal in the deposits, and which has a larger lattice constant than the metal in the deposits. Examples of metals for metal exchange include gold, silver, copper, platinum, palladium and nickel. Under metal-exchanging conditions, the exposed metal of the deposits undergo metal exchange with the less electropositive metal, forming deposits of surface-enhanced-Raman-active metal, capped with deposits of a second surface-enhanced-Raman-active metal which is less electropositive and has a higher lattice constant.

Additionally, the method can comprise contacting the substrate with surface-enhanced-Raman-active metal nanoparticles. These metal nanoparticles are functionalized with ligands to link the nanoparticles to the deposits. This contact can be performed after differentially removing a portion of the first material or with no such removal.

Further, the method can comprise associating the surface-enhanced-Raman-active metal deposits with a target analyte or a specific recognition molecule where the specific recognition molecule specifically reacts with a target analyte, for example by binding to it either covalently or non-covalently. For example, using a precursor to a SERS active substrate made of PAO with arrays of silver nanowires filling the pores of the PAO, one can prepare this substrate to detect BRCA-1 (the gene encoding breast cancer type 1 susceptibility protein) by binding the exposed tips of the silver nanowires with an oligonucleotide complimentary to a portion of one strand of this gene. The oligonucleotide must be substituted with an appropriate silver-binding group, such as a thiol or amine. After the nucleotide has been attached to the tips of the silver wires, the substrate can then be washed and hermetically sealed in plastic. Providing a precursor to a SERS active substrate ready to detect the presence or absence of BRCA-1 in a sample.

Additionally, the method can comprise creating a substrate with nanoholes at the tips of the nanowires. This can be accomplished by, for example, by depositing a nanoparticle in each of the pores of a porous matrix of a first material, wherein the pores of this porous matrix are closed on one end. (The nanoparticle is sometimes referred to herein as a third material, with the matrix and SERS-active metals being first and second materials, respectively).Following deposition of these nanoparticles, the pores of the matrix are filled with a SERS-active metal deposits, where the metal being deposited is different from the material of the nanoparticle. The matrix material is then differentially removed from the closed pore side of the matrix, exposing the nanoparticles and the tips of the SERS-active metal nanowires. The nanoparticle material is then differentially removed relative to the tip of the SERS-active metal nanowires, leaving a depression in the nanowire tip and thus forming a nanohole in the tip of the nanowire. The resulting substrate then includes SERS-active metal nanowires having nanoholes at the nanowire tips.

Methods of Analysis

The present disclosure also provides methods for determining the presence or absence of an analyte in a sample comprising:

i) treating a substrate comprising:
    a porous matrix of a first material, wherein the pores of said matrix are nanometer in scale, wherein the distance between the pores is nanometer in scale and wherein the pores are filled with deposits of a surface-enhanced-Raman-active metal, wherein this treating provides at least two surface-enhanced-Raman-active metal positioned a distance from each other suitable for generating a 'hot spot' surface enhanced Raman spectroscopy signal, wherein at least one of these surfaces is on a deposit of surface-enhanced-Raman-active metal at least partially imbedded in the substrate, ii) contacting the substrate with the sample, and iii) detecting a surface enhanced Raman spectrum (SERS) signal;

wherein the SERS signal is indicative of the presence or absence of the analyte.

It will be appreciated that the detecting step generally involves exposing the substrate to surface enhanced Raman spectrum-generating conditions. Generally, the SERS spectrum generated is collected and the collected spectrum examined for at least one Raman signal characteristic of the presence or absence of the analyte in the sample.

The distance between pores in the first material can range from about 10 nanometers apart to about 200 nanometers apart. A variety of metals are surface-enhanced-Raman-active, including lithium, sodium, potassium, platinum, indium, copper, silver and gold.

The substrate may be packaged in or protected by an environmental protection agent. If the substrate is protected by such an agent, the agent should be removed from the substrate before additional treatment. If the agent is in the form of a film or covering on the substrate, that film may be removed by any method which does not damage the underlying substrate. For example, if the agent is a polymeric film, this film can be dissolved in an appropriate solvent. The substrate may need to be rinsed to remove this solvent from the substrate before further treatment.

The substrate can be treated prior to contacting the substrate with the sample ("treat then contact"). Additionally, the substrate can be contacted with the sample prior to treatment ("contact then treat").

The substrate can also be treated by differentially removing the first material to expose the surface-enhanced-Raman-active metal deposits as nanowires. When these nanowires are sufficiently exposed from the first material, the tips of these nanowires can spatially condense to a smaller distance than the distance between the pores of the matrix. The distance achieved should be suitable for generating a 'hot spot' SERS signal.

The pores in the template can be widened appropriately or closely spaced pores are produced by appropriate choice of template-fabrication conditions so as to create nanowires that are very closely spaced without the need for prolonged etching of the matrix. In the pore-widening approach, templates with widely-spaced pores are produced and widened in an appropriate etching solution, which for aluminum oxide might be phosphoric acid or a chromic/phosphoric solution or an alkali solution such as aqueous sodium, potassium or ammonium hydroxide or sodium or potassium carbonate, or another suitable etchant, so as to create pores which are sufficiently closely spaced to bring the sides of the metal nanowires appropriately closely together. In this embodiment no further etching need be used to create SERS-active interstices between the nanowires.

Substrates comprising nanowires with nanoparticles of a material different from that of the nanowire (and usually different from that of the matrix) imbedded in the tips of these nanowires may be treated by differentially removing the nanoparticles from the nanowire tips, e.g., by etching. Where differential removal is by etching, this may be accomplished in the same or different etching conditions as removal of the matrix material. This differential removal forms nanoholes in the tips of the nanowires of the substrate. The surfaces defining these nanoholes are in proximity sufficient to generate a SERS signal.

The substrate may be treated by exposing the tips of the metal deposits, and then subjecting the exposed tips to metal exchange with a surface-enhanced-Raman-active metal which is less electropositive than the metal in the deposits and has a larger lattice constant than the metal in the deposits. Because the exchanged metal has a larger lattice constant, the resulting surface-enhanced-Raman-active metal nanostructures are more closely spaced than the pores in the first material. The distance between metal nanostructures should be suitable for generating a 'hot spot' SERS signal.

For example, if the initial deposits in the first material are copper, and the exposed copper tips are converted to silver by metal exchange in a silver-ion containing solution, such as aqueous silver nitrate, the resulting silver nanostructures will be more closely spaced than the original copper deposits were.

Further, the substrate may be treated by exposing the substrate to nanoparticles of surface-enhanced-Raman-active metal nanoparticles which are functionalized with appropriate ligands, for example alkane dithiol derivatives. These ligands link the nanoparticles to the deposits of surface-enhanced-Raman-active metal in the substrate.

Treatment with surface-enhanced-Raman-active metal nanoparticles can also be performed upon substrates where the first material has been differentially removed, for example by etching, so that the deposits of surface-enhanced-Raman-active metal have been exposed as nanowires.

The analyte may contact the substrate via specific recognition molecules associated with the surface-enhanced-Raman-active metal. These specific recognition molecules specifically react with a target analyte, for example by binding to that analyte. The functionality of the specific recognition molecule is selected so as to be capable of a unique molecular recognition function towards the analyte. For example, if the targeted analyte is a gene, then a short single-stranded oligonucleotide complimentary to a portion of one of the strands of that gene sequence may be used to specifically bind with that gene. In this example, the oligonucleotide should be terminated with a group capable of binding to the surface-enhanced-Raman-active metal, for example a thiol or amine group. Other examples of specific recognition molecules which can be used are molecules which form host-guest complexes with the target analyte.

In general, the substrate can be contacted with the sample by exposing the substrate to a fluid sample (e.g., gas, liquid, etc.). For example, any analytes present can bind to specific recognition molecules associated with the metal deposits in the substrate, where they can then be detected by SERS. As another example, the sample may simply be brought into physical contact with the metal deposits in the substrate. Analytes in this sample then adsorb onto the metal deposits, where they can then be detected by SERS.

It will be appreciated that the methods of analysis can also involve intermediate wash steps as may be desirable. For example, after contacting with the sample, it may be desirable to wash away unbound sample. In addition, the method of analysis can involve analysis of treated substrate at different time points. This can be accomplished by, for example, washing away the etching solution to stop further removal of matrix material at a desired time point, then using these treated substrates for SERS analysis.

In general, Raman spectrum generating conditions involve illumination of the substrate with monochromatic light in the visible, near-IR or near-UV range. Methods of use can include exposing SERS-active substrate to be analyzed (e.g., one with which a sample of interest has been contacted) to Raman-spectrum generating conditions, collecting Raman spectra, and examining the spectra collected to assess the presence or absence of the analyte.

EXAMPLES

The following examples illustrate various aspects of exemplary embodiments of the present invention, and are not intended to limit the scope of the invention set forth in the claims appended hereto.

Example 1

Making a Silver/Porous Aluminum Oxide Substrate

Certain embodiments of the present invention are related to a sensing platform for performing surface-enhanced Raman spectroscopy using arrays of metallic nanowires. FIG. 1 illustrates an exemplary method used for the preparation of silver nanowire embedded in porous aluminum oxide (Ag-PAO) and the manner in which it was treated so as to render it a SERS-active substrate. PAO was electrochemically fabricated on high purity (99.99%) aluminum sheet in 0.3 M oxalic acid using Masuda's two-step anodization process (FIG. 1, panels (i) through (iii), Masuda, H.; Fukuda, K. *Science* 1995, 268, 1466-1468.) The anodization was carried out at 40 V D.C. at 15-17° C. A one-hour second anodization step resulted in an anodic alumina template with nano-channel depth of about 5 μm. To reduce the thickness of the barrier layer facilitating Ag deposition, a third anodization was carried out in 0.2 M phosphoric acid for 10 min under the same conditions. This was followed by pore-widening in 0.1 M phosphoric acid at 40° C. for 40 min (FIG. 1, panel iv). Ag deposition was carried out at room temperature by AC electrolysis in Ag electrolyte of 0.05 M $AgNO_3$+0.5 M $H_3BO_3$ (FIG. 1, panel v). Based on scanning electron microscope (FEI XL40, Sirion) measurements, the average pore-diameter was about 70 nm, the average distance between pores was about 100 nm, the average spacing between wires was about 30 nm, and the average aspect ratio of the resulting Ag-PAO substrate was about 70 nm.

Example 2

Add Analyte then Etch Analysis vs. Etch then Add Analyte Analysis

In order to produce a clean and uniformly Ag-filled surface for SERS spectroscopy, the Ag-filled PAO (Ag-PAO) template was epoxy-glued to a silicon wafer oxide-side down and the aluminum on the backside of Ag-PAO was removed by etching in saturated aqueous $HgCl_2$ for 1 h (FIG. 1, panels (vi) to (vii). The alumina matrix of the resulting Ag-PAO templates was then partially etched in 0.1 M aqueous NaOH for 10 min to expose the tips of Ag nanowires (FIG. 1, panel (viii)). The templates were then dipped in 1 mM an ethanolic benzenethiol (BT) solution for 10 min. The foregoing describes what we will refer to as the add-analyte-then-etch method (FIG. 1, scheme (a)). The BT-modified Ag-PAO templates were then immersed in 0.1 M NaOH solution for variable lengths of time from 30 to 450 s in 30 s intervals. Before each Raman measurement, the template was taken out of the etchant and washed with distilled water and dried under ambient condition. The sample was then returned to the etchant for further etching after the Raman spectrum was recorded. For SEM imaging a separate batch of experiments was carried out under the same conditions.

In the "etch-then-add-analyte" method (FIG. 1, scheme (b)), Ag-PAO templates (made as described above in this Example) were etched in a 0.1 M NaOH solution for variable lengths of time from 30 to 330 s in 30 s intervals, and from 330 s to 450 s in 60 s intervals (producing 13 etched Ag-PAO samples in all). Each of the samples was then functionalized with BT in a 1 mM of ethanolic BT solution for 10 min (FIG. 1, scheme (b)).

Backscattered Raman spectra were recorded on a LabRam microRaman system (Jobin-Yvon/ISA) equipped with a thermoelectrically cooled CCD detector. Spectra were excited using the 514.5-nm line of a cw Ar ion laser (SpectraPhysics 164). The incident laser beam was focused, and the Raman signal was collected using a×100 objective with an NA of 0.80. Approximately 0.7 mW of laser irradiation was used to excite the samples. The signal collection time was 60 sec.

Figure 2A:
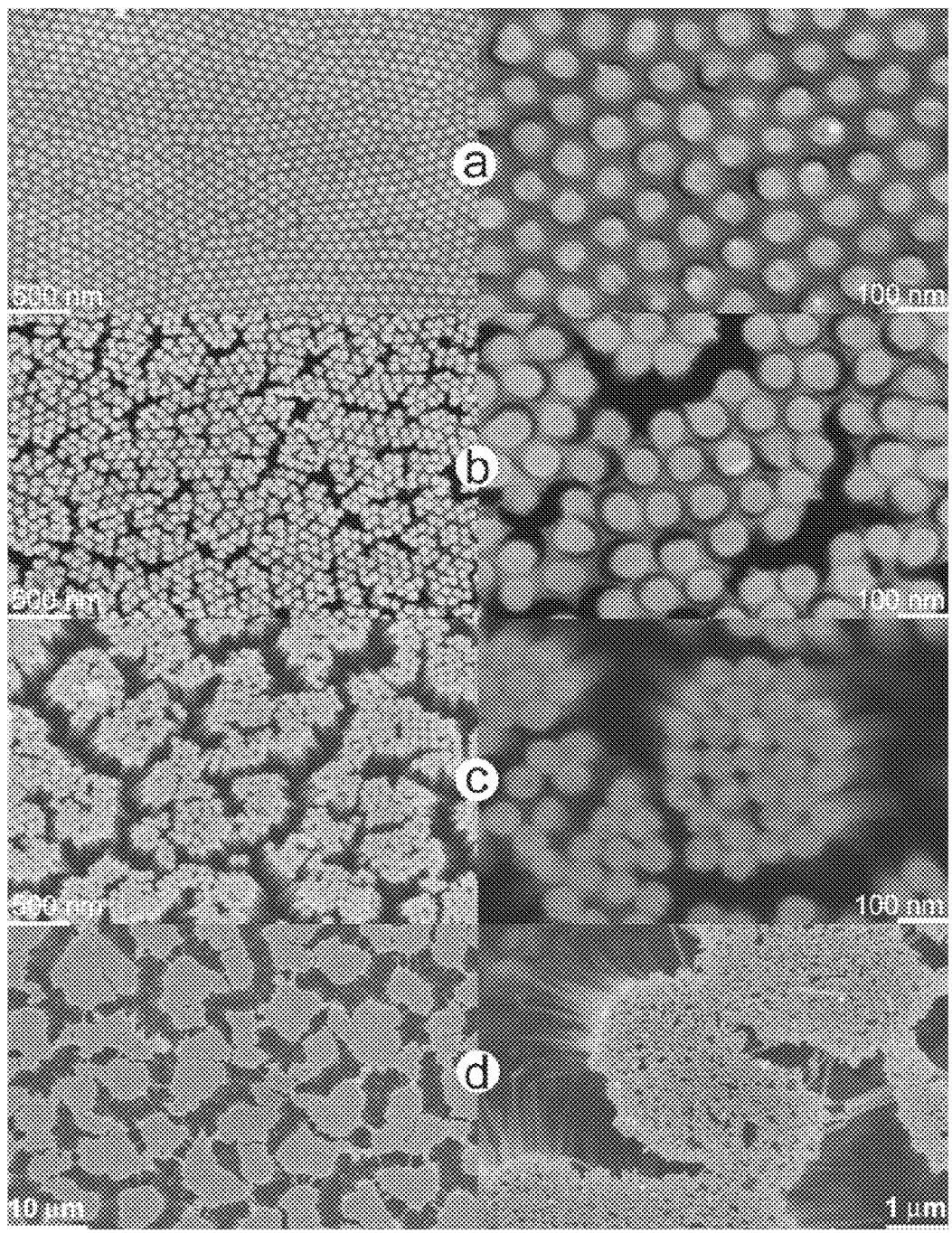
FIGS. 2A-2C.
Figure 2B:
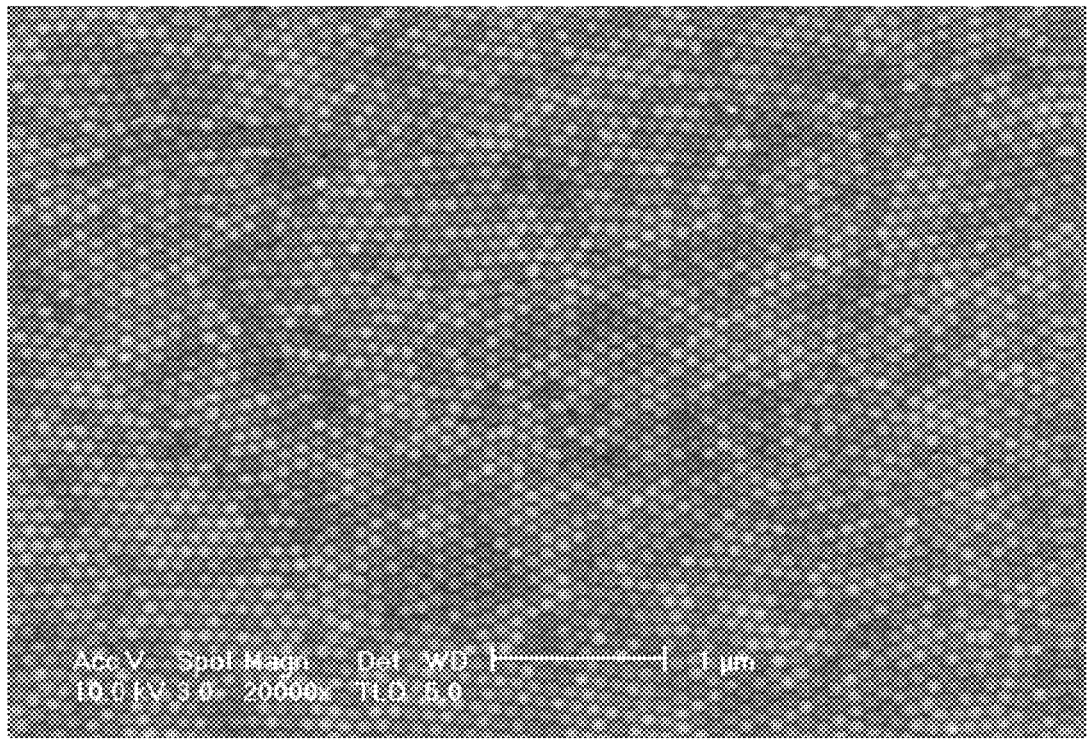
Figure 2C:
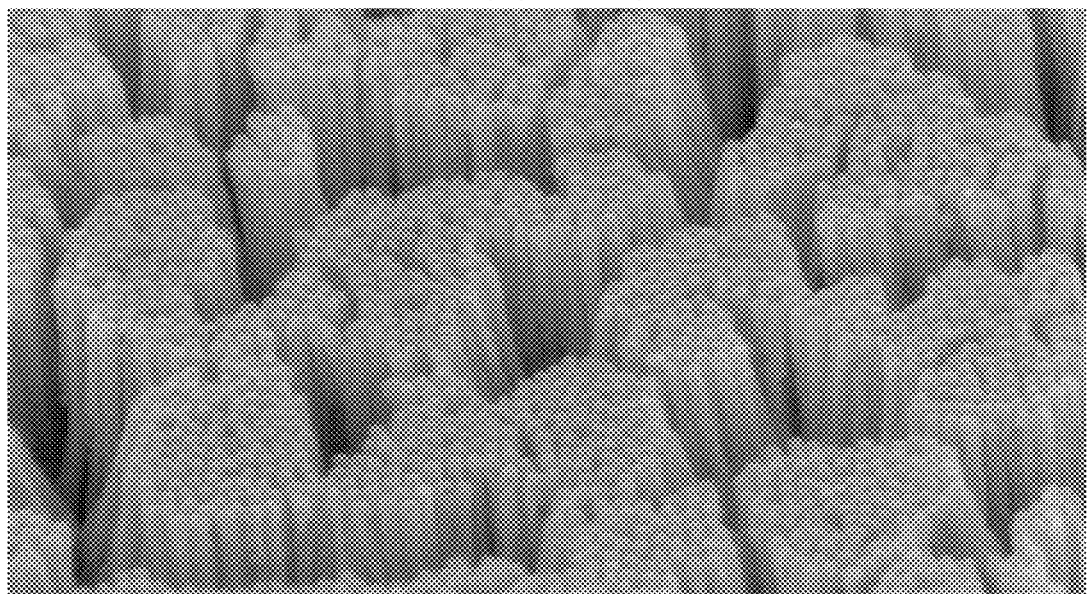
Figure 3:
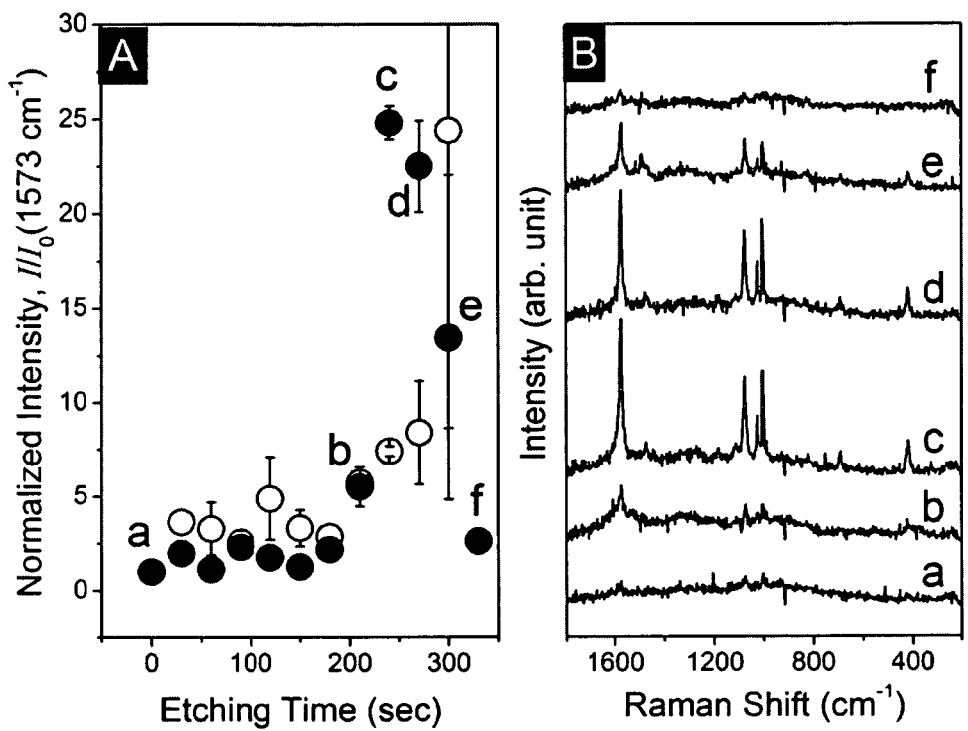
FIG. 3. Panel A: Normalized intensities of the 1573 $cm^{-1}$ band plotted as a function of the etching time at 30 s intervals; filled circles correspond to the add-analyte-then-etch example; the open circles to the etch-then-add analyte example. Points (a)-(f) correspond to the normalized intensities of the SERS spectra acquired after 0 s, 210 s, 240 s, 270 s, 300 s, and 330 s, respectively. Panel B: Selected SERS spectra, obtained in the add-analyte-then-etch example. Spectra (a)-(f) correspond to the various etching times indicated by points (a)-(f) in (A).

FIGS. 2A-2C provide SEM images of BT-modified AG-PAO substrates made by the add-analyte-then-etch method. FIG. 3, Panel A is a graph normalized intensities of the 1573 $cm^{-1}$ band plotted as a function of the etching time at 30 s intervals. As discussed in more detail below, the filled circles correspond to results from the add-analyte-then-etch method and the open circles correspond to results from the etch-then-add analyte method. Points (a)-(f) correspond to the normalized intensities of the SERS spectra acquired after 0 s, 210 s, 240 s, 270 s, 300 s, and 330 s, respectively. FIG. 3, Panel B is a graph of selected SERS spectra, obtained in the add-analyte-then-etch method. Spectra (a)-(f) correspond to the various etching times indicated by points (a)-(f) in FIG. 3, Panel A.

Examining the results of the add-analyte-then-etch method first, FIG. 2A, panel (a) and FIG. 2B show the SEM image of BT-exposed Ag-PAO before the etching process was carried out. The tips of Ag nanowires protrude slightly above the oxide matrix. At this point the SERS signal is very weak (FIG. 3, panel (B), spectrum (a)). SEM images of (BT-covered) Ag nanowire tips are shown as a function of etching time in aqueous 0.1 M NaOH in FIG. 2A, panels (b) through (d). FIG. 2C provides an SEM image of the sample as in FIG. 2A, panel (c), but imaged at a glancing angle. The corresponding intensity of the 1573 $cm^{-1}$ SERS band as a function of etch time as well as representative SERS spectra are also displayed in FIG. 2, Panel A (filled circles) and FIG. 3, Panel B, respectively. At the early stages of the etching process (up to about 210 s), pore-widening of the PAO template is observed accompanied by a slight increase in the protrusion of the Ag nanowires above the alumina matrix (FIG. 2A, panel (b)). At this stage, the gap between tips of neighboring nanowires is about 20 nm, implying that the EM gap fields is still rather weak. And indeed, at the beginning of the etching process an almost unchanging and weak SERS signal is observed (FIG. 3, panel (B), spectrum (a)), so long as the silver nanowires are unable to bend sufficiently so as to reduce the inter-nanowire gap.

After about 270 s of etching, a sufficient length of the nanowire is freed from its matrix to allow the tips of the nanowires to bend towards each other forming closely interacting bundles thereby trapping and automatically positioning analyte molecules pre-adsorbed at the tips of the nanowires in the junctions between neighboring tips. Recalling the aforementioned fact that electromagnetic 'hot spots' tend to be gap modes in the interstice between closely-spaced metallic nanostructures, intense EM field enhancement is expected for this tip/analyte/tip arrangement. The SERS spectra, in fact, show a significant (about 25×) intensity increase over its initial value at this point (FIG. 3, panel (B), spectra (c) and (d)).

As the etching progresses to about 450 s, the sizes of bundles continue to grow, but the SERS intensity decreases and eventually is undetectable (FIG. 3, panel (B), spectra (e) and (f)). This abrupt decrease in SERS intensity might be due to the reduction in the integrity of the tip-to-tip geometry when the last of alumina matrix is etched away reducing the stability of the nanowire bundles, as they begin to lose their anchor in the alumina template (FIG. 2A, panel (d)). It is estimated that on average about 80 nanowires are illuminated by the laser. Assuming that on each nanowire the analyte covers a hemispherical cap with about 35 nm radius, it is estimated that at most about $3.3 \times 10^{-18}$ mol (i.e., about 2.0×

$10^6$ molecules) are being sampled by the laser in the add-analyte-then-etch methods. Further, only a fraction of these molecules occupy gap sites between the almost-touching nanowire tips.

In the etch-then-add-analyte method, the SEM images were much the same as those shown in FIG. 2A after etching for equivalent lengths of time. The dependence of the SERS intensities on etching time differ, however, from what was observed in the former set (FIG. 3, panel (A), open circles). Even after about 240 s of etching the SERS intensities remain relatively weak and reached the intensity levels of the add-analyte-then-etch method after about 300 s of etching. Moreover, the SERS intensity did not decrease on further etching but reached a saturation value after about 450 s of etching at which point the SERS intensity is about 50× the initial value (i.e. the value observed after only moderate etching). At this point the maximum SERS intensity achieved in the two methods is approximately equal (within a factor of 2) even though in the former set only the tips of the nanowires were coated with analyte, while in the latter, the entire length of the nanowire (about 5 μm) is covered with analyte, implying that the average enhancement achieved in the add-analyte-then-etch approach exceeds that in the etch-first-then-add-analyte approach by at least a factor of about $1.3 \times 10^2$. Without being held to theory, this may be due to the difference in the production methods. In the add-analyte-then-etch approach, many analyte molecules will be positioned within the gaps created by the collapsing nanowire tips, and therefore benefit from the giant electromagnetic fields that exist in those hot spots. In the etch-then-add-analyte approach, the molecules adsorb along the entire lengths of the nanowires and thus are present in hot clefts and gaps that have formed to a lesser degree than in the add-analyte-then-etch approach. Moreover, the availability of gaps might be reduced by the fact that without the molecular species pre-adsorbed on the nanowires most nanowires will touch upon their collapse making the gap inaccessible to the analyte.

Example 3

Observing SERS while Etching

Figure 4:
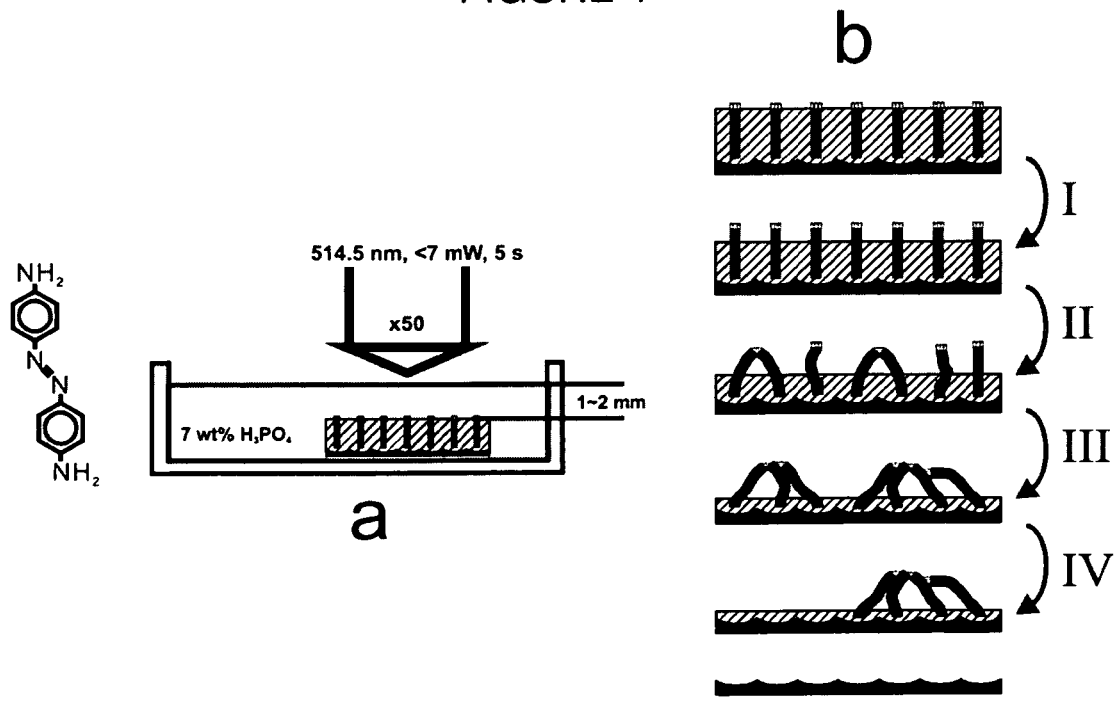
FIG. 4. Schematic drawing illustrating a technique described in the disclosure but with the open side of the pore being interrogated while the sample is etched continuously in phosphoric acid. Panel (a): schematic of the cell in which progressive etching is carried out while the SERS spectrum is simultaneously measured. Panel (b): the sample is composed of silver nanowires embedded in the alumina matrix in which they were fabricated whose tips have been exposed to the analyte (4,4 diaminoazobenzene, DAAB). Panel (b), step I shows that as etching progresses the nanowire tips are exposed and remain spatially separated by the matrix material. Panel (b), step II shows that as etching progresses further the nanowire tips collapse together forming the hot-spots with the analyte sandwiched within them. Panel (b), step III shows that as etching progresses further, the nanowires condense into bundles. Panel (b), step IV shows that as etching progresses further, the nanowires start to release from the alumina framework. Eventually the alumina framework is dissolved and the system washes away. The process can optionally be slowed or halted when an optimal SERS signal is achieved.
Figure 5:
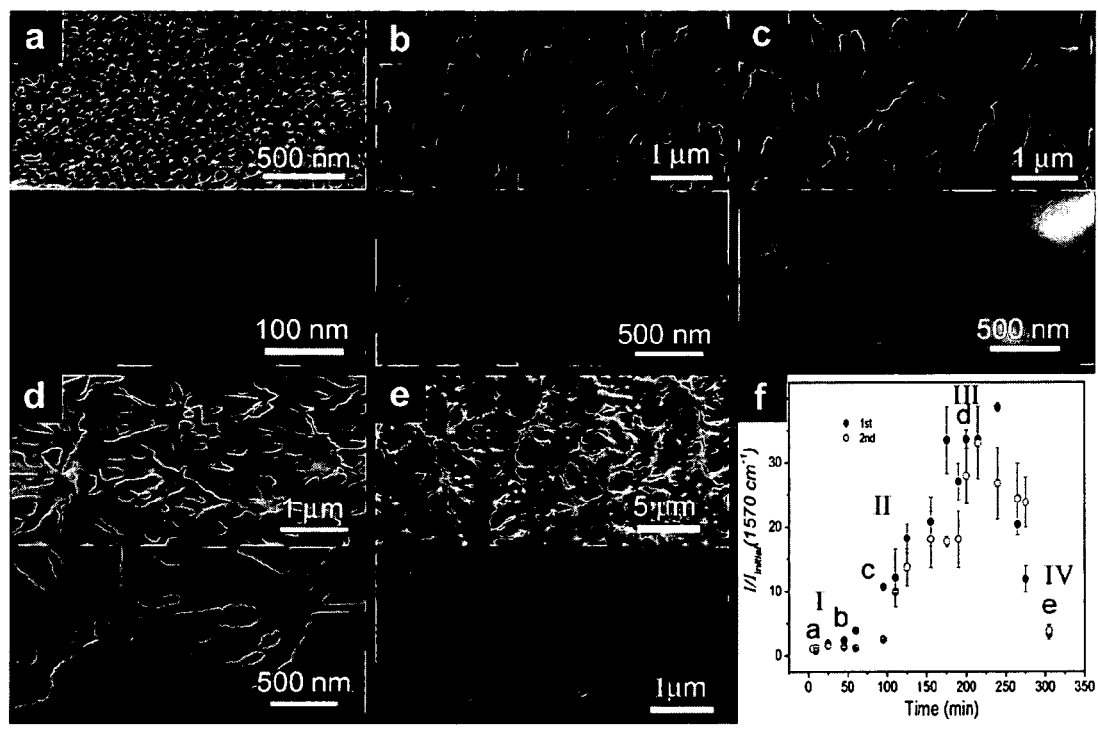
FIG. 5. Correlation of the SERS intensity with SEM images obtained by etching the open-side of Ag-PAO template. The SEM images collected are shown in FIG. 5, panels (a) through (e), where the lower portion of each panel is a 5× magnification over the upper portion of each panel. Panel (a) shows the surface of the substrate prior to treatment. Panel (b) shows the surface of the substrate after about 45 minutes of etching. Panel (c) shows the surface of the substrate after about 90 minutes of etching. Panel (d) shows the surface of the substrate after about 200 minutes of etching. Panel (e) shows the surface of the substrate after about 300 minutes of etching. Panel (f) shows the normalized intensity of the 1570 cm$^{-1}$ band of DAAB, with respect to etching time. In panel (f) the closed and open circles correspond to results from two different methods. The closed circles correspond to the add-analyte-then-etch method, while the open circles correspond to the add-analyte then etch method.
Figure 6:
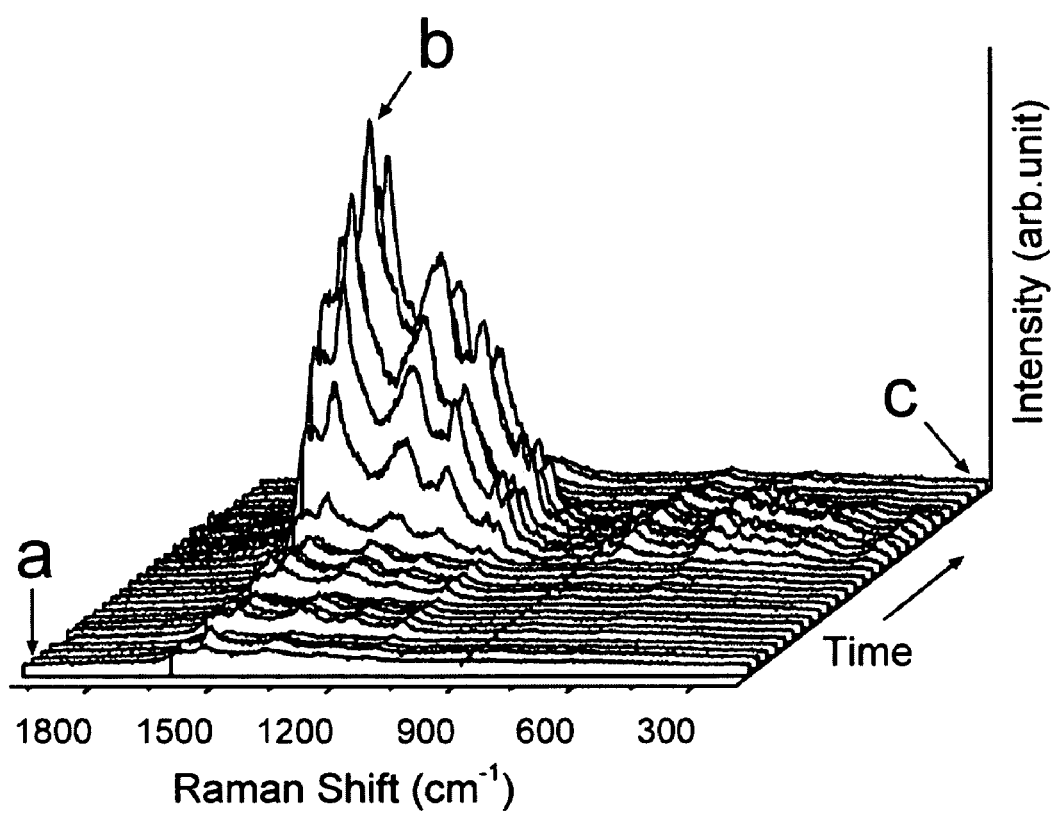
FIG. 6. SERS spectra recorded as a function of etching time for samples prepared as illustrated in FIG. 4. At the beginning of the etching process the silver nanowires stand substantially straight so that their tips are separated one from another and the SERS spectrum is weak, as shown in spectrum (a). As the etching process continues the matrix in which the nanowires reside is dissolved away and the tips collapse together under the effect of Van der Waals forces forming SERS hot spots, as shown in spectrum (b). When etching progresses too far, the system begins to collapse and the SERS signal decreases, as shown in spectrum (c).

Another approach to etching and analyte analysis is illustrated in FIGS. 4-6. The tips of the nanowires of Ag-filled PAO template are functionalized with diaminoazobenzene (DAAB, shown at left in FIG. 4, panel (a)), which serves as the analyte in for purposes of this example, at the open end of the pores. The template is etched continuously in phosphoric acid while the SERS spectrum is recorded. FIG. 4, panel (a) shows a schematic of the method used, where the substrate is shown open-pore side up, with 1-2 mm of nanowires exposed. These exposed nanowire tips are functionalized with DAAB analyte. The substrate is then immersed in 7% phosphoric acid and SERS spectra are taken while etching occurs. FIG. 4, panel (b) shows a representation of the nanowires' conformation as etching continues. Step (I) of panel (b) shows that as etching begins, the nanowires remain vertical and widely separated. As etching continues the nanowires begin to spacially condense forming 'hot-spots' as shown in step (II). As etching continues the nanowires form larger and larger bundles as shown in step (III). As etching progresses even further, some of the nanowires begin to lose contact with the matrix, as shown in step (IV). Eventually, all of the aluminum oxide is etched away, leaving only the aluminum backing of the substrate, shown in the bottom illustration of panel (b).

In this add-analyte-then-etch example with DAAB analyte attached to the nanowire tips, the etching process is stopped at the desired time point as set out below, the samples washed with distilled water then dried and the SEM image of the etched template obtained. Alternatively, this approach is modified to provide an etch-then-add-analyte approach in which the template is first etched to expose the nanowires before the analyte (DAAB) is adsorbed on the nanowires' surface.

The SEM images collected from the add-analyte-then-etch method using the functionalized DAAB are shown in FIG. 5, panels (a) through (e), where the lower portion of each panel is a 5× magnification over the upper portion of each panel. Panel (a) shows the surface of the substrate at the beginning of the method. Panel (b) shows the surface of the substrate after about 45 minutes of etching. Panel (c) shows the surface of the substrate after about 90 minutes of etching. Panel (d) shows the surface of the substrate after about 200 minutes of etching. Panel (e) shows the surface of the substrate after about 300 minutes of etching. Panel (f) of FIG. 5 shows the normalized intensity of the SERS spectra, with respect to time for both the add-analyte-then-etch and the etch-then-add-analyte methods. In panel (f) the open and closed circles represent results obtained from by two separate methods. The closed circles correspond to data from add-analyte-then-etch example, while the open circles correspond to data from add-analyte then etch example. The points labelled (a) through (e) in panel (f) correspond to SERS spectra collected after the same etching time as the SEM images in panels (a) through (e), respectively.

FIG. 6 shows a stack plot of the spectra collected from the add-analyte-then-etch method using functionalized DAAB analyte. At the beginning of the etching process the silver nanowires stand straight so that their tips are separated one from another and the SERS spectrum is weak, as shown in spectrum (a). As the etching process continues the matrix in which the nanowires reside is dissolved away and the tips collapse together under the effect of Vander Waals forces forming SERS hot spots, as shown in spectrum (b). When etching progresses too far, the system collapses and the SERS signal decreases and eventually is undetectably, as shown in spectrum (c).

Example 4

Preparing a Packaged Substrate for Affinity Recognition SERS Analysis

This example describes the use of a substrate comprising of a matrix of porous aluminum oxide (PAO), wherein the pores are filled are filled with deposits of silver.

This example begins with a substrate precursor having a removable protective cover (e.g., such as may be provided by packaging or by a removable protective layer on one or more surfaces of the substrate precursor). To prepare a sample for analysis, the substrate is separated from its removable protective cover and treated so as to produce as SERS-active substrate. Production of the SERS-active substrate from the precursor can be accomplished according to any of the method discussed herein. For example, the SERS-active substrate can be produced by differential remove of the matrix material, matrix material of the substrate is etched in an appropriate etching solution such as phosphoric acid, a chromic/phosphoric solution, or an alkali solution such as aqueous sodium hydroxide, potassium hydroxide, ammonium hydroxide, sodium carbonate, or potassium carbonate for a desired period. For example, the substrate can be exposed to the etching solution of a time sufficient to remove an amount of aluminum oxide matrix material to provide for exposure of the SERS metal nanowires either to approach each other closely or to fall together forming clusters of nanowires, but not for so long as to allow the metal nanowires to lose their anchor within the remaining aluminum oxide anchor. Alternatively, where SERS analysis is conducted over time, etching may be allowed to continue over an entire period that includes loss of nanowire anchoring, e.g., so as to facilitate identification of a SERS spectrum peak. The treated substrate is then rinsed in distilled water, alcohol or any other suitable rinsing agent or agents and a suitable functionality is added to the surface of the nanowires so as to contact all or a portion of the exposed metal surface.

The functionality is appropriately selected so as to be capable of a unique molecular recognition function towards the analyte. For example, if the targeted analyte is a polynucleotide (e.g., corresponding to a gene of interest, e.g., a genomic DNA, mRNA or cDNA), then a short single-stranded oligonucleotide appropriately terminated with a functional group (e.g., a thiol or amine) so as to facilitate binding to the metal. The oligonucleotide is chosen so that it will be complementary to a portion of one of the strands of the target polynucleotide of interest. Alternatively one can dilute the molecule possessing the desired molecular-recognition functionality in a mixture with an inert substance that will nevertheless passivate those areas of the surface-enhanced-Raman-active metal which are not functionalized, thereby protecting the metal from adsorption by contaminants. In this example, the inert substance acts as a "blocking agent" to reduce false positives that may result from non-specific binding and/or contaminants. The sample (e.g., fluid (gas or liquid)) suspected of containing the analyte is then added to the substrate and Raman analysis is carried out. All of these steps can be automated and carried out sequentially within a simple machine.

Alternatively, one can permute several of the preceding steps (i through v) as is required or convenient to the desired analysis, for example, the surface functionality can be added to the surface before etching is carried out. Likewise, where the substrate has a side having exposed pores (e.g., the "open side") and an opposite side on which the pores are partially or completely covered by matrix material (e.g., the "closed side") the substrate can be oriented in the etching solution so that either side is "face up" in the etching solution. Stated differently, either side of such a substrate precursor can be oriented so as to provide for etching to expose the metal nanowires for functionalization and etching as may be desired.

Example 5

Biomolecular Sensing Using Oligonucleotides as Specific Recognition Molecules

The following illustrates an example of use of the substrates described herein in the detection of a biomolecular analyte.

Figure 7:
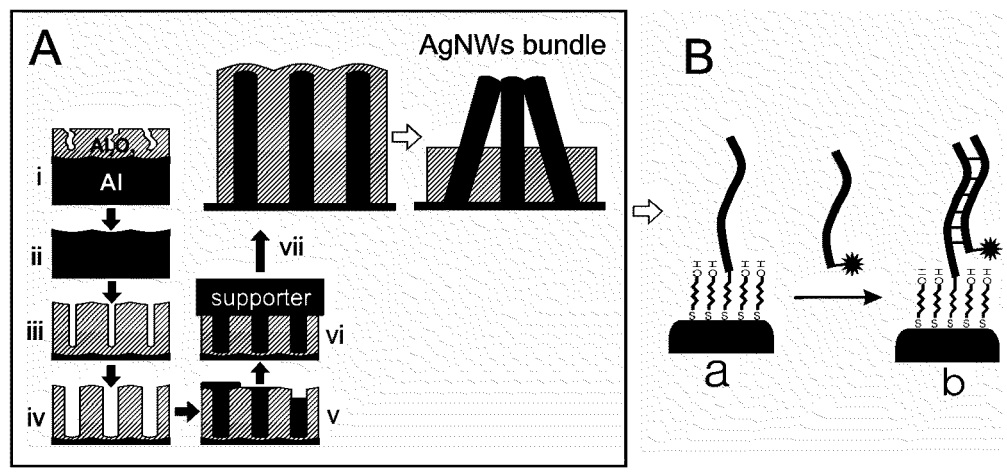
FIG. 7. Schematic illustration for (Panel A) the preparation of array of SERS-active silver nanowire (AgNWs) bundles and (Panel B) its subsequent application for the detection of DNA hybridization. In Panel B, (a) illustrates a SERS-active substrate having probe-DNA modified AgNWs bundles and (b) illustrates hybridization of a target complementary nucleic acid target analyte, which is optionally with labeled with a detectable dye.
Figure 8:
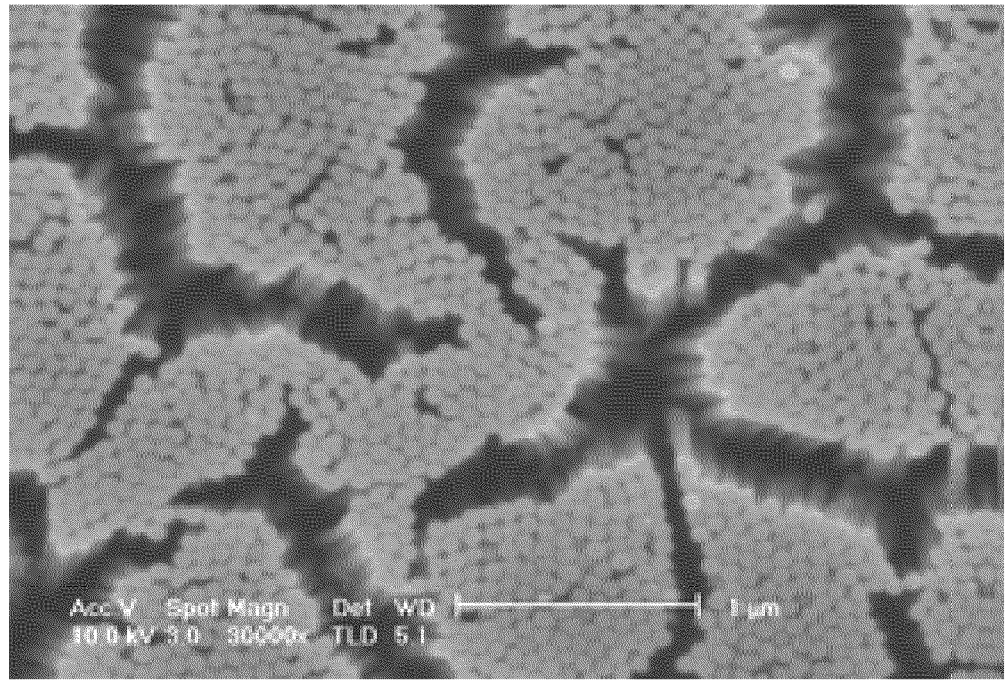
FIG. 8. A representative SEM image of SERS-active AgNWs bundles of SERS-active substrates formed using the method exemplified in FIG. 7.

The method used for the preparation of silver nanowire embedded in porous aluminum oxide and the manner in which it was treated so as to render it a SERS-active substrate is shown schematically in FIG. 7. PAO was electrochemically fabricated on a high purity (99.99%) aluminum sheet in 0.3 M oxalic acid using Masuda's two-step anodization process (Masuda, H.; Fukuda, K. Science 1995, 268, 1466-1468.) (see FIG. 7, panel A, i through iii). The anodization was carried out at 40 V d.c. at 15-17° C. A second anodization step lasting one-hour resulted in a template with nanopore depth of about 5 μm. To reduce the thickness of the barrier layer facilitating silver deposition, a third anodization was carried out in 0.2 M phosphoric acid for 10 min under the same conditions. This was followed by pore-widening in 0.1 M phosphoric acid at 40° C. for 40 min (FIG. 7, Panel A, iv). Silver deposition was carried out at room temperature by AC electrolysis in an Ag electrolyte solution (0.05 M $AgNO_3$+0.5 M $H_3BO_3$) (FIG. 7, Panel A, v). Based on scanning electron microscope (FEI XL40, Sirion) measurements on this substrate, the average pore-diameter was about 70 nm, the average inter-pore distance was about 100 nm, the average inter-wires-spacing was about 30 nm, and the average aspect-ratio was about 70 nm.

The Ag-filled PAO (Ag-PAO) substrate was epoxy-glued to a silicon wafer (oxide-side down) and the aluminum on the backside of Ag-PAO was removed by etching in saturated aqueous $HgCl_2$ for one hour. (FIG. 7, Panel A, vi to vii) The alumina matrix of the resulting Ag-PAO templates was then partially etched 0.1 M aqueous NaOH to form SERS-active silver nanowire bundles, thus producing SERS-active substrates. (FIG. 7, Panel A, viii)

20-mer oligonucleotides were synthesized (Operon, HPLC purified). The sequences of these oligionucleotides are summarized in Table 1.

TABLE 1

Oligonucleotide Sequences Used

| Strand Label | Sequence |
|---|---|
| A | HS-$(CH_2)_6$-5'-CATCAGCTCAACCTCTCTCA-3' (SEQ ID NO: 1) |
| a'-F | 5'-TGAGAGAGGTTGAGCTGATG-3'-[Fluorescein] (SEQ ID NO: 2) |
| a' | 5'-TGAGAGAGGTTGAGCTGATG-3' (SEQ ID NO: 2) |

A buffer solution was prepared by dissolution of sodium phosphate (10 mM) and sodium nitrate (100 mM) in ultrapure water (resistivity>18.0 MΩcm) at pH 7.4. The SERS-active substrates were exposed to a 2 μM solution of the probe-a strand (a-AgNWs) in this buffer for 3 hours. The a-strand functionalized SERS-active substrates (a-AgNWs) were then immersed in 1 mM of aqueous 6-mercapto-1-hexanol (MCH) solution for 1 hour. This solution was used to prevent non-specific binding of DNA on the silver nanowires and to improve hybridization efficiency to the complementary strand. The a-AgNWs were then washed with water and dried under $N_2$ stream. The resulting a-AgNWs were incubated with 2 μM of either target-a' or target-a'-F solutions at 36° C. for 3 h, then washed several times with buffer solution and briefly with water. The hybridized surfaces were dried under $N_2$ stream and then subjected to Raman measurement under ambient conditions. Backscattered Raman spectra were recorded on a LabRam microRaman system (Jobin-Yvon/ISA) equipped with a thermoelectrically cooled CCD detector. Spectra were excited using the 514.5-nm line of a cw Ar ion laser (SpectraPhysics 164). The incident laser beam was focused, and the Raman signal was collected using a×100 objective with an NA of 0.80. Approximately 0.7 mW of laser irradiation was used to excite the samples. The signal collection time was 120 sec.

Figure 9:
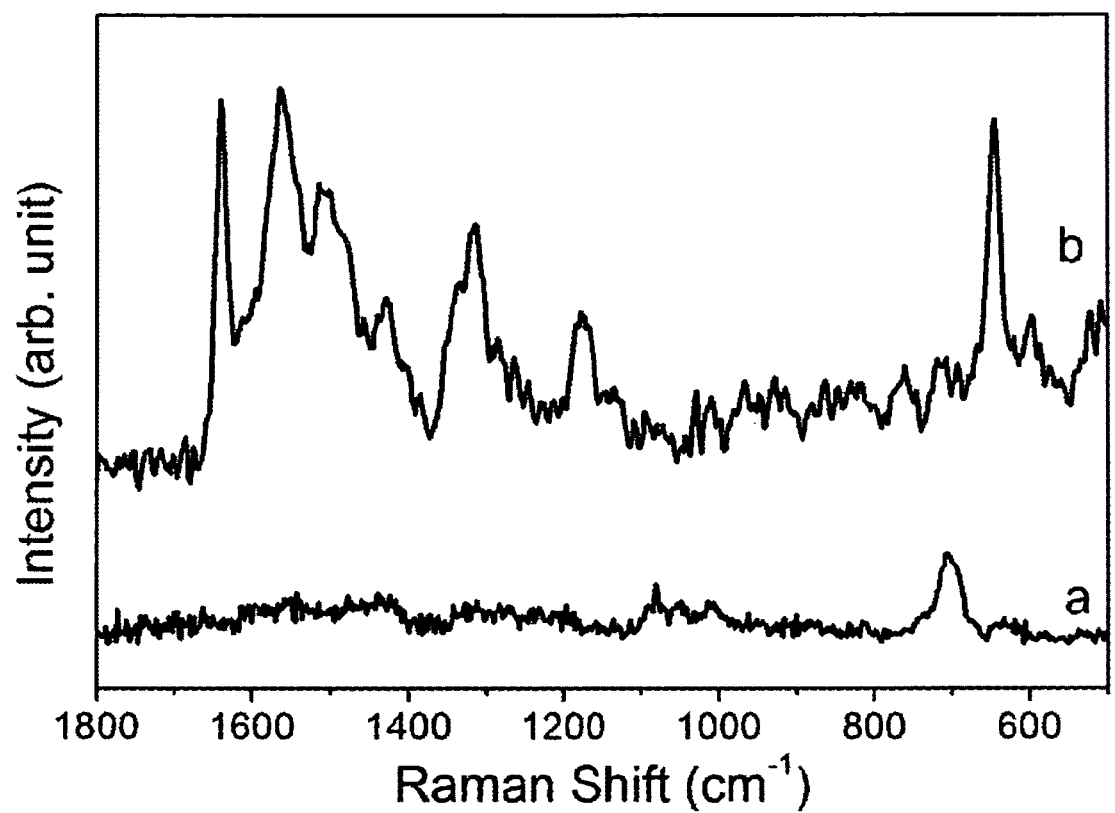
FIG. 9. Exemplary SERS spectra of (a) a-AgNWs and (b) aa'-F—AgNWs of Example 5.

FIG. 9, trace a shows the SERS spectrum of a-AgNWs. There are intense Raman band observed at ~700 $cm^{-1}$ which is assignable to C-S stretching mode from HS-DNA and MCH. After hybridization with a'-F distinct spectral features are observed and assignable to F (FIG. 9, trace b) In the hybridization with a', new spectral features also were observed but not distinct than those of aa'-F—AgNWs. Assuming a DNA density of about <6×10$^{-12}$ mol/cm for the thiolated DNA/MCH self-assembled monolayers (as previously reported for gold film (Lay, R. Y. Et al. Langmuir 22, 10796-10800 (2006)) it can be concluded that about a few thousand DNAs residing within the laser spot area gave rise to the signals. Thus, detection using a specific recognition molecule (strand a) to detect a specific analyte (strand a'-F) has been shown.

Example 6

Control of Inter-Nanowire-Gap-Distance for Substrates

A series of periodic SERS-active Ag nanowires embedded in highly ordered porous aluminum oxide were fabricated, in which the inter-wire gap-distance was varied from 35 nm to 10 nm. The SERS response of a probe molecule introduced into the gaps of these systems was measured at 514.5 nm and 785 nm. At 785 nm the SERS intensity varied by a factor of more than 200 on going from 35 to 10 nm.

Figure 10:
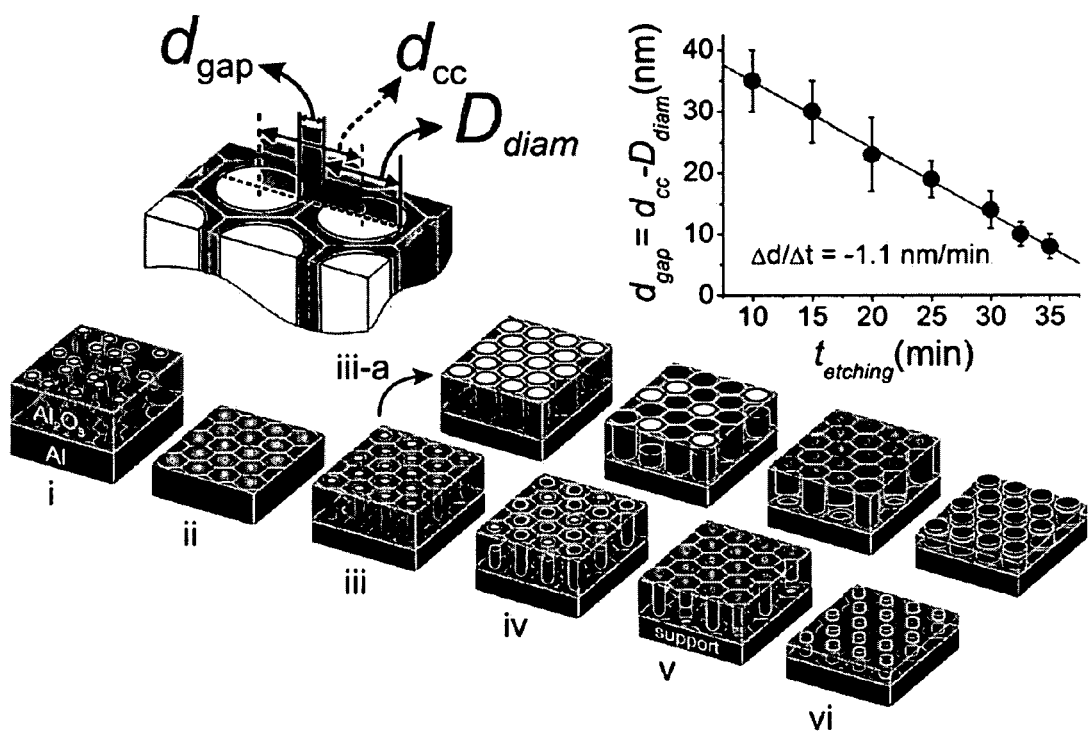
FIG. 10. Schematic illustrating the fabrication of SERS systems consisting of periodically disposed Ag nanowires embedded in highly-regular porous aluminum oxide (PAO) templates with varying inter-wire gap distances, $d_{gap}$. PAO were electrochemically fabricated on aluminum sheet in 0.3 M oxalic acid using Masuda's two-step anodizing process (i through iii). This was followed by pore-widening in 0.5 M phosphoric acid (iii to iii-a). Pore-widening was carried out so as to create templates with $d_{gap}$ values of 35±5, 30±5, 23±6, 19±3, 14±3, 10±2, and 8±2 nm. The etching rate ($\Delta d_{gap}/\Delta t_{etch}$) was experimentally found to be ~1.1 nm/min (Inset). Ag deposition was carried out at room temperature by AC electrolysis (iv). The Ag-PAO samples were epoxy glued to a Si wafer (oxide-side down) and the aluminum on the backside of Ag-PAO was removed by etching in saturated $HgCl_2$ for 1 h (iv to v). The alumina matrix surrounding the silver nanowires was partially etched in 0.1 M aqueous NaOH for ~10~12 min to expose approximately 50 nm the tips of AgNWs (vi).
Figure 11:
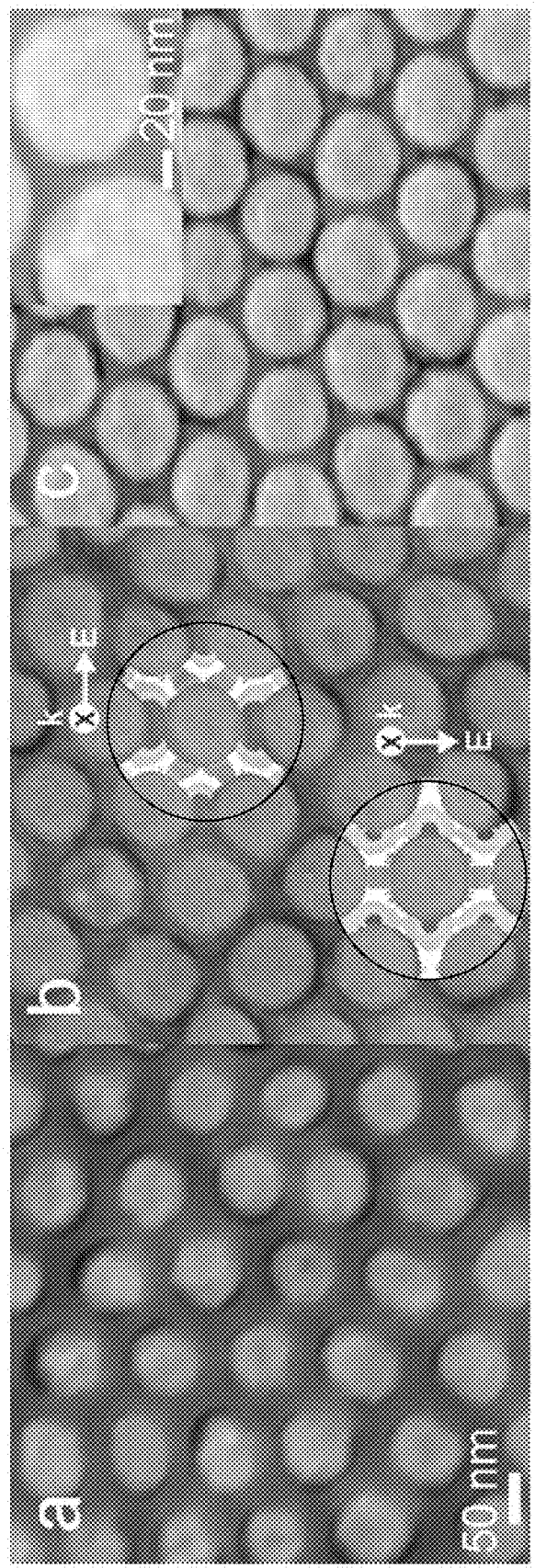
FIG. 11. SEM images (FEI XL 40) of Ag-PAO templates with dgap of (Panel a) 35±5, (b) 19±3, and (c) 10±2 nm. (The 50 nm scale bar applies to all three images.) The calculated local EM fields amplitude in the vicinity of a central nanodisc surrounded by six hexagonally-arranged discs are superimposed on the SEM figures in (Panel b). The parameters $d_{gap}$=20 nm, $D_{diam}$=80 nm, and λex=785 nm were assumed in the calculation; k and E indicate, respectively, the wavevector and electric vector directions of the incident light. Inset in (Panel c) shows a magnification of a portion of the image shown in (Panel c).

Periodic 2-D arrays of silver nanowires (AgNWs) with good wire-to-wire diameter reproducibility and periodic domains extending over areas tens of square micrometers, were electrochemically produced in porous aluminum oxide (PAO) templates. The inter-nanowire gaps were theoretically predicted to be SERS hot spots whose enhancing ability can be varied systematically and dramatically using template-assisted control of the inter-wire spacing (Masuda, H.; Fukuda, K. *Science* 1995, 268, 1466-1468; Al-Mawlawi, D.; Liu, C. Z.; Moskovits, M. *J. Mater. Res.* 1994, 9, 1014-1018.) This strategy is schematically illustrated in FIG. 10. Prior to AgNW deposition, the PAO templates were etched in 0.5 M phosphoric acid at 40° C. for a variable time resulting in pores of progressively larger (but uniform) diameter and a decreasing pore-wall thickness between pores. SEM images of three of the experimental samples with inter-wire gap distances of (a) $d_{gap}$ (35 nm), (b) $d_{gap}$ (19 nm), and (c) $d_{gap}$ (10 nm) are shown in FIG. 11. The high order, hexagonal periodicity is clearly visible. The simultaneous variation of the nanowire diameter, $D_{diam}$, and $d_{gap}$ is not a problem since both parameters are purely geometrical factors and both are appropriately considered in the calculations.

Figure 12:
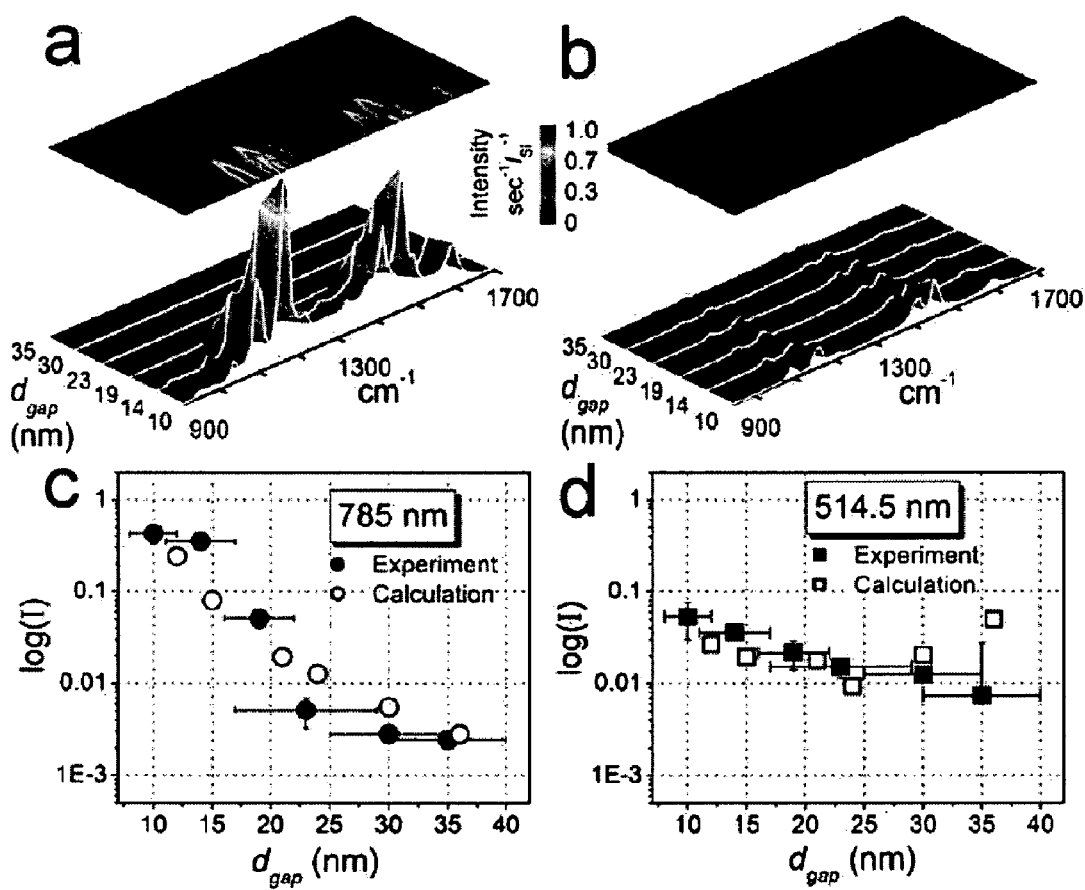
FIG. 12. SERS spectra and corresponding 2-D intensity contour maps of 4-aminobenzenethiol (4-ABT) adsorbed on the Ag-PAO nanoarrays are shown as a function of dgap. Spectrum and 2-D contour map excited with (Panel a) 785 nm and with (Panel b) 514.5 nm. The prominent bands observed at 1580, 1438, 1390, 1142, and 1078 cm-1 are due to benzene ring vibrations. The Si band at 520 cm-1 was used as a calibration marker to correct for the spectrometer's response at the two wavelengths. Experimentally-measured (filled points) and calculated (open points) intensities of the 1078 cm-1 SERS line of 4-ABT plotted as a function of the inter-wire gap size are shown in (Panel c) and (Panel d), respectively, for 785 and 514.5 nm excitation. Logarithms of the intensities are plotted so as to compress the intensity scale. The error bars for the Log(I) scale is shown for those points for which the error exceeds the size of the point.

FIG. 12 panels (a) and (b) show the SERS spectra of 4-ABT recorded as a function of $d_{gap}$. At 785 nm excitation the SERS intensity increases dramatically as the $d_{gap}$ decreases. The dependence on gap size is less pronounced when the nanostructure is excited with 514.5 nm. For example, with 514.5 nm excitation the SERS intensity at 1078 cm$^{-1}$ decreases by a factor of ~7 on going from $d_{gap}$=10 nm to $d_{gap}$=35 nm. By contrast 785 nm excitation the SERS intensity decreased by a factor of ~200 on going from the former to the latter sample. These observations agree well with the calculated values at both excitation wavelengths (FIG. 12 panels (c) and (d)). This agreement is better for red ($\lambda_{ex}$=785 nm) excitation than for green ($\lambda_{ex}$=514.5 nm).

Overlaid on the SEM image in FIG. 11 panel (b) are contour maps of the calculated local EM field amplitudes in the vicinity of a group of seven 80 nm diameter (i.e., $d_{gap}$=20 nm) cylinders simulated at two orthogonal polarizations and $\lambda_{ex}$=785 nm. Although the location of the hot spots changes with the polarization of the incident light used, the EM enhancements averaged over all of the surfaces of the nanostructures was approximately constant, independent of the polarization. This situation differs from what is expected for one or a few molecules localized, for example, in the interstices between two nanoparticles where polarization is expected to be a significant factor determining SERS enhancement.

Example 7

Nanowires with Nanoholes to Optimize SERS Enhancement

A SERS-active substrate consisting of an ordered, 2-dimensional array of nanoholes that allow strong SERS signals was fabricated and tested. The precisely controlled geometry also allows for the study of the signal enhancements of anisotropic nanostructures and thus to optimize SERS enhancements for sensing applications.

Figure 13:
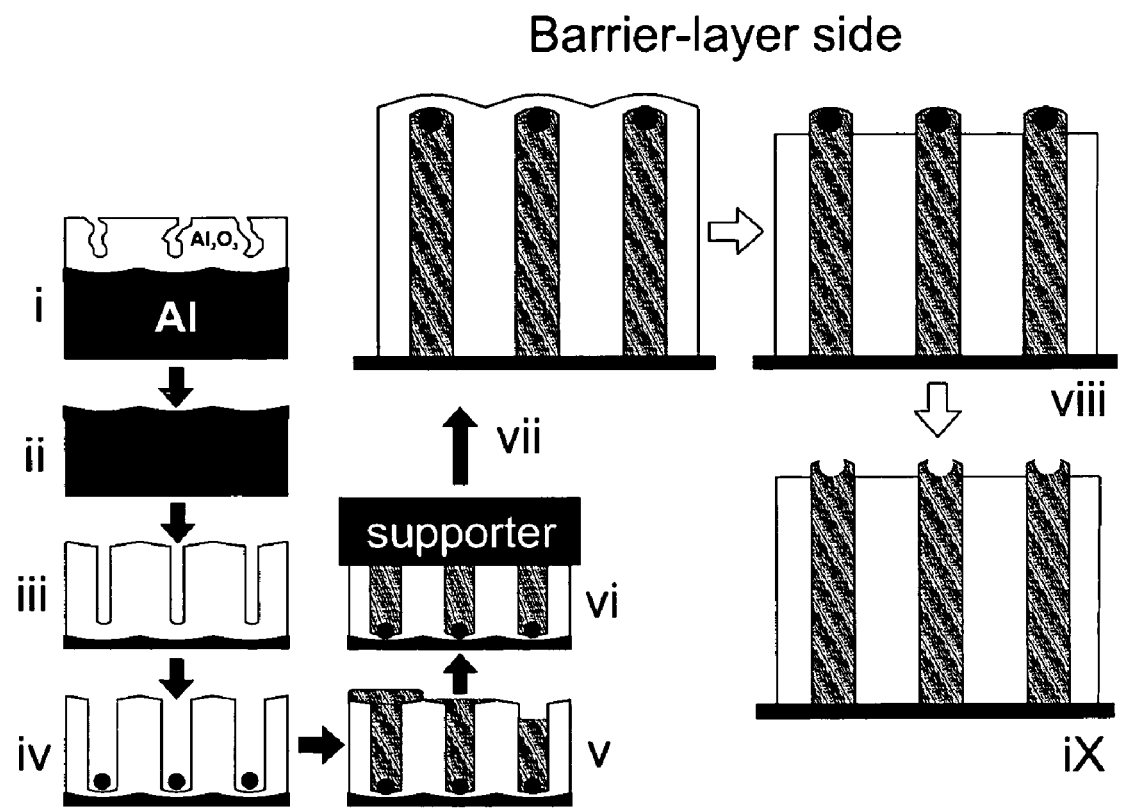
FIG. 13. Schematic illustration for an exemplary method of fabricating nano-hole array using a Ag-PAO template.

This embodiment is similar to the array of Ag nanowires embedded in porous aluminum oxide template, except the tips of nanowires are modified to produce nano-sized hole for maximal SERS enhancement. Ag nanowires each containing a nanohole at the tip were fabricated in highly-ordered, porous aluminum oxide (PAO) and then exposed by controllably removing the alumina matrix (FIG. 13). Copper nanoparticles about 40 nm across were synthesized by AC electrolysis in a solution containing 0.05M Cu(NO$_3$)$_2$ and 0.5M H$_3$BO$_3$ at 17V$_{ac}$ (sine wave, 20 Hz) for 15 sec. The AC frequency and time of deposition were chosen so as to form only a small copper particle at the bottom of each pore. Ag was further deposited using an Ag electrolyte solution (0.05 M AgNO$_3$+0.5 M H$_3$BO$_3$) which sealed all but the bottom of the nanoparticles in silver. The substrate was then mounted on a Si wafer and the aluminum removed with saturated, aqueous HgCl$_2$. In order to expose the SERS active regions, the back side of the template (i.e. the barrier layer side) was partly etched with 0.1 M sodium hydroxide for about 12 min and then copper nanoparticles were etched with 0.1 M ferric chloride for about 5 min.

Figure 14:
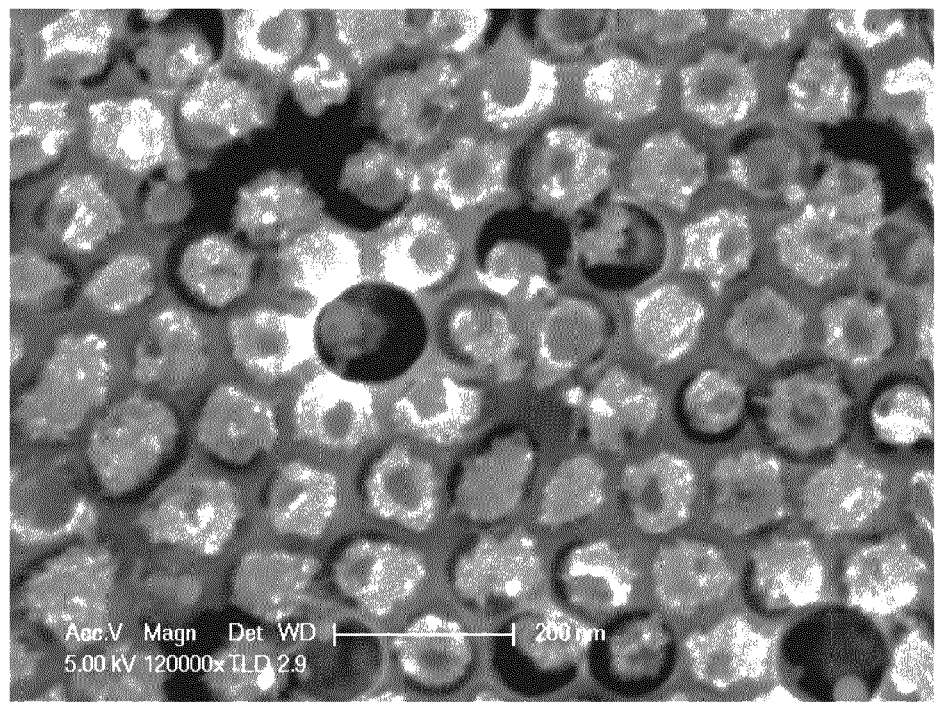
FIG. 14. Exemplary SEM image of Ag nanowires array containing a nanohole at the tips (top panel) and its corresponding SERS response (bottom panel). In the bottom panel, the bottom trace is SERS spectrum obtained from Ag nanowire array without nanoholes; the upper traces are SERS spectra obtained from Ag nanowire array with nanoholes at three different points. SERS spectra were taken under 514.5 nm, 0.7 mW, and 30 s.
Figure 14:
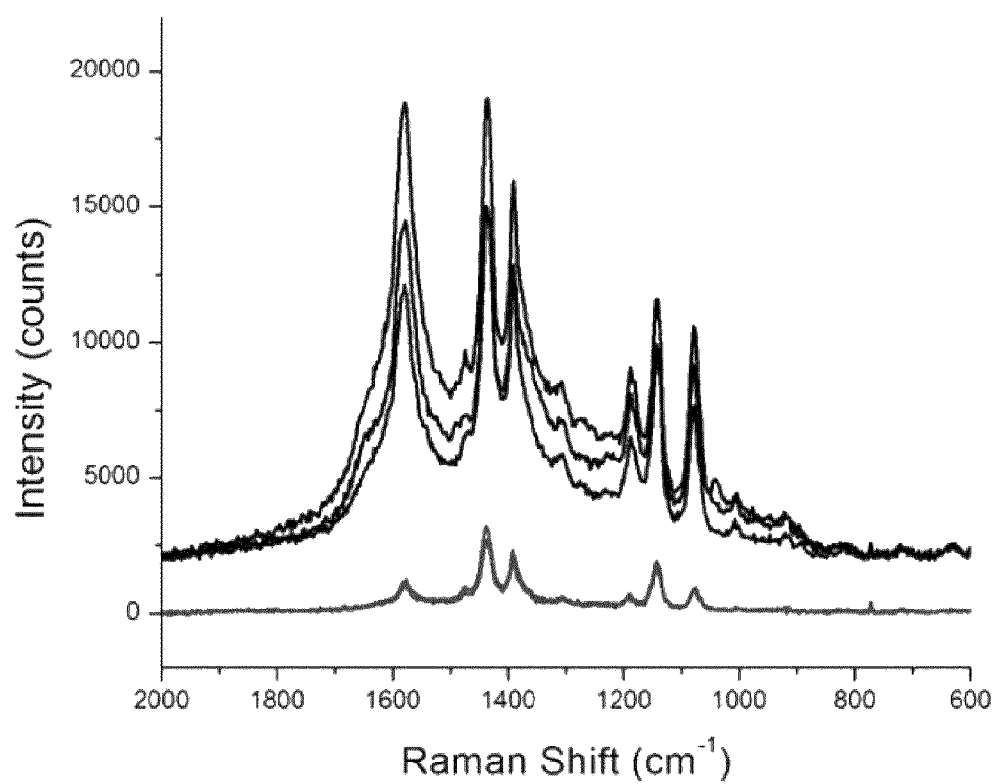

FIG. 14 top panel shows an SEM image of Ag nanowire array, where each nanowire has a nanohole at the tip. The SERS activity of the template was evaluated by applying an ethanolic solution of 4-aminobenzenethiol (ABT) to the sample. The SERS signal intensity was reproducibly observed to be about 10-15 time higher than that of a Ag nanowire array without nanoholes. In cross-sectional view (FIG. 13), the shape of the resulting nanowire resembles a crescent nano-moon with sharp tips, and in top view the shape of the structure resembles a nano-ring with a higher sharpness than the previously demonstrated, so the circular sharp edge of this structure can have a stronger field emitting or antenna effect. Since the Ag nanowire array containing nanoholes has of both nanotip and nanoring geometrical features on the sharp edge region, a significant EM field enhancement is expected.

Certain aspects of this invention provide a strategy for obtaining SERS-active substrates, which contain 'hot spots' of the form 'metal/molecule/metal', which automatically positions analytes in the junction between neighboring tips of metallic nanowires fabricated in an appropriate porous template or matrix such as aluminum oxide (PAO) then exposed by the controlled dissolution of the matrix. The process is highly reproducible in part because the steps followed in fabricating the SERS-active substrate is closely prescribed yielding reproducible substrates and in part because of the regularity of the SERS substrate, which comprises highly-ordered and regular arrays of nanowires sealed in a template or a matrix. Because the nanowires are encapsulated in the pores of the matrix this system is potentially immune to contamination until it is ready for use, at which point the matrix is etched thereby allowing the nanowires to collapse into bundles and form hot spots in the regions of close contact between the nanowires, trapping of the analyte in those junctions.

What is claimed is:

1. A method of analysis to determine the presence or absence of an analyte in a sample comprising:
  i) treating a substrate comprising:
    a porous matrix of a first material defining a first surface, wherein the pores of said matrix are nanometer in scale, wherein the distance between the pores is nanometer in scale, and wherein the pores are filled with deposits of a surface-enhanced-Raman-active metal, and wherein the deposits are covered with an additional layer defining a second surface;
    wherein said treating comprises differentially removing said first material to expose said surface-enhanced-Raman-active metal as nanowires, and wherein said nanowires are capable of spatially condensing to a distance of separation which is smaller than the distance between pores of the matrix and suitable for generating a surface enhanced Raman spectroscopy signal;
  ii) contacting said substrate with a sample suspected of containing an analyte;
  iii) detecting a surface enhanced Raman spectrum (SERS) signal;
  wherein the SERS signal is indicative of the presence or absence of the analyte.

2. The method of analysis according to claim 1, wherein said treating comprises forming an indentation in the tips of said nanowires.

3. The method of analysis according to claim 1, wherein said treating comprises etching said first material to widen said pores.

4. The method of analysis according to claim 3, such that the distance between pores is reduced so as to condense the distance separating the subsequently-deposited surface-enhanced-Raman-active metal to a distance of separation which is smaller than the distance between pores of the matrix prior to etching.

5. The method of analysis according to claim 1, wherein said treating comprises:
  exposing the tips of said deposits, and
  subjecting said exposed tips to metal exchange with a surface-enhanced Raman spectroscopy-active metal which is less electropositive than the metal in said deposits and has a larger lattice constant than the metal in said deposits.

6. The method of analysis according to claim 1, wherein said treating comprises exposing said substrate to SERS-active metal nanoparticles, wherein said nanoparticles are functionalized with ligands, wherein said ligands link said nanoparticles to said deposits of surface-enhanced Raman spectroscopy-active metal in said substrate.

7. The method of analysis according to claim 6, wherein said first material of said substrate is differentially removed to provide exposed nanowires of said surface-enhanced Raman spectroscopy-active metal prior to exposing said substrate to said nanoparticles.

8. The method of analysis according to claim 1, wherein said contacting is performed prior to said treating.

9. The method of analysis according to claim 1, wherein said treating is performed prior to said contacting.

10. The method of analysis according to claim 1, wherein said analyte contacts said substrate via specific recognition molecules associated with said surface-enhanced Raman spectroscopy-active metal, wherein said specific recognition molecules specifically react with said analyte.

11. A substrate comprising:
  i) a porous matrix of a first material defining a first surface, wherein the pores of said matrix are nanometer in scale, wherein the distance between the pores is nanometer in scale, and wherein the pores are filled with deposits of a surface-enhanced-Raman-active metal; and
  ii) an additional layer defining a second surface, which is opposite the first surface and covers said deposits,
  wherein differential removal of said first material from said deposits exposes said surface-enhanced-Raman-active metal as nanowires capable of spatially condensing to a distance of separation which is smaller than the distance between pores of the matrix.

12. The substrate according to claim 11, wherein said first material is differentially removable from said deposits of a surface-enhanced-Raman-active metal.

13. The substrate according to claim 12, wherein said first material is differentially etchable from said deposits of a surface enhanced Raman spectroscopy-active metal.

14. The substrate according to claim 11, wherein said pores are elongate.

15. The substrate according to claim 14, wherein said elongate pores have an aspect ratio of at least 10.

16. The substrate according to claim 11, wherein the metal is chosen from the group consisting of silver, gold, copper, platinum and indium.

17. The substrate according to claim 11, wherein said substrate comprises a target analyte associated with the metal.

18. The substrate according to claim 11, wherein said substrate comprises a specific recognition molecule associated with the metal, wherein said specific recognition molecule specifically reacts with a target analyte.

19. The substrate according to claim 11, comprising an agent capable of isolating said substrate from environmental hazards.

20. The substrate according to claim 11, comprising surface-enhanced-Raman-active metal nanoparticles linked to said deposits via ligands.

21. The substrate according to claim 11, wherein said deposits of surface-enhanced-Raman-active metal are capped with deposits of a second surface-enhanced Raman spectroscopy-active metal, wherein said second surface-enhanced Raman spectroscopy-active metal deposits are more closely spaced than said pores.

22. The substrate according to claim 11, wherein said deposits of a surface-enhanced-Raman-active metal extend beyond the surface of the first material.

23. The substrate according to claim 22, wherein said deposits of a surface-enhanced-Raman-active metal extend beyond the surface of the first material as surface-enhanced-Raman-active metal nanowires.

24. The substrate according to claim 22, wherein the metal is chosen from the group consisting of silver, gold, copper, platinum and indium.

25. The substrate according to claim 23, wherein said substrate comprises a target analyte associated with the metal.

26. The substrate according to claim 23, wherein said substrate comprises a specific recognition molecule associated with the metal, wherein said specific recognition molecule specifically reacts with a target analyte.

27. The substrate according to claim 23, comprising an agent capable of isolating said substrate from environmental hazards.

28. The substrate according to claim 23, wherein the substrate comprises nanowires having a tip defining a nanohole.

29. A method of making a substrate comprising:
   i) filling the pores of a porous matrix of a first material with nanometer scale deposits of surface-enhanced-Raman-active metal, wherein said pores are nanometer in scale, wherein the distance between said pores is nanometer in scale, and wherein said first material defines a first surface;
   ii) covering the deposits with an additional layer defining a second surface; and
   iii) differentially removing a portion of said first material thereby exposing said nanometer scale deposits of surface-enhanced-Raman-active metal as nanowires, wherein said nanowires are capable of spatially condensing to a distance of separation which is smaller than the distance between pores of the matrix.

30. The method according to claim 29, comprising contacting said substrate with surface-enhanced-Raman-active metal nanoparticles, wherein said nanoparticles are functionalized with appropriate ligands linking said nanoparticles to said deposits.

31. The method according to claim 29, comprising associating a target analyte with said metal.

32. The method according to claim 29, comprising associating a specific recognition molecule with said metal, wherein said specific recognition molecule specifically reacts with a target analyte.

33. The method according to claim 29, comprising exposing said substrate to conditions appropriate for metal exchange with a surface-enhanced-Raman-active metal which is less electropositive than the metal in said deposits and has a larger lattice constant than the metal in said deposits.

34. The method according to claim 29, comprising contacting said substrate with surface-enhanced-Raman-active metal nanoparticles, wherein said nanoparticles are functionalized with appropriate ligands linking said nanoparticles to said deposits.

35. The method according to claim 29, comprising associating a target analyte with said metal.

36. The method according to claim 29, comprising associating a specific recognition molecule with said metal, wherein said specific recognition molecule specifically reacts with a target analyte.

37. The method according to claim 29, wherein nanoparticles are deposited into the pores prior to said filling.

38. The method according to claim 29, wherein the substrate comprises nanoparticles positioned within exposed tips of said nanowires, wherein the nanoparticles are removed to produce a nanohole in the exposed tips.

\* \* \* \* \*

UNITED STATES PATENT AND TRADEMARK OFFICE
CERTIFICATE OF CORRECTION

| | |
|---|---|
| PATENT NO. | : 7,898,658 B2 |
| APPLICATION NO. | : 12/018763 |
| DATED | : March 1, 2011 |
| INVENTOR(S) | : Martin Moskovits, Seung Joon Lee and Ioana Pavel |

It is certified that error appears in the above-identified patent and that said Letters Patent is hereby corrected as shown below:

At Column 1, beginning at line 5, please insert the following paragraph between the title and the CROSS REFERENCE TO RELATED APPLICATIONS heading:

--This invention was made with Government support under Grant No. DAAD19-03-D-0004, awarded by the Army/ARO. The Government has certain rights in this invention.--

Signed and Sealed this
Nineteenth Day of April, 2011

David J. Kappos
*Director of the United States Patent and Trademark Office*